United States Patent
Perkins et al.

(10) Patent No.: US 10,555,100 B2
(45) Date of Patent: Feb. 4, 2020

(54) ROUND WINDOW COUPLED HEARING SYSTEMS AND METHODS

(75) Inventors: Rodney C. Perkins, Woodside, CA (US); Sunil Puria, Sunnyvale, CA (US)

(73) Assignee: Earlens Corporation, Menlo Park, CA (US)

(*) Notice: Subject to any disclaimer, the term of this patent is extended or adjusted under 35 U.S.C. 154(b) by 158 days.

(21) Appl. No.: 12/820,776

(22) Filed: Jun. 22, 2010

(65) Prior Publication Data

US 2011/0152602 A1    Jun. 23, 2011

Related U.S. Application Data

(60) Provisional application No. 61/219,286, filed on Jun. 22, 2009.

(51) Int. Cl.
H04R 25/00 (2006.01)
(52) U.S. Cl.
CPC ................ H04R 25/606 (2013.01)
(58) Field of Classification Search
CPC ...... H04R 25/00; H04R 25/60; H04R 25/606; A61F 2002/183
USPC ...... 600/25, 126; 381/23.1, 312, 68; 607/55, 607/56, 57, 137; 181/129
See application file for complete search history.

(56) References Cited

U.S. PATENT DOCUMENTS

| | | |
|---|---|---|
| 3,209,082 A | 9/1965 | McCarrell et al. |
| 3,440,314 A | 4/1969 | Eldon |
| 3,449,768 A | 6/1969 | James |
| 3,549,818 A | 12/1970 | Turner |
| 3,585,416 A | 6/1971 | Mellen |
| 3,594,514 A | 7/1971 | Wingrove |
| 3,710,399 A | 1/1973 | Hurst |

(Continued)

FOREIGN PATENT DOCUMENTS

| | | |
|---|---|---|
| CN | 1176731 A | 3/1998 |
| CN | 101459868 A | 6/2009 |

(Continued)

OTHER PUBLICATIONS

Ayatollahi, et al. Design and Modeling of Micromachined Condenser MEMS Loudspeaker using Permanent Magnet Neodymium-Iron-Boron (Nd—Fe—B). IEEE International Conference on Semiconductor Electronics, 2006. ICSE '06, Oct. 29 2006-Dec. 1 2006; 160-166.

(Continued)

Primary Examiner — Samuel G Gilbert
(74) Attorney, Agent, or Firm — Wilson Sonsini Goodrich and Rosati, P.C.

(57) ABSTRACT

A support can be configured for placement in the middle ear to couple a transducer to the round window, such that the transducer can be removed from the round window without damaging the round window. The support can be configured to couple the transducer to the sound window such that the support can be removed from the round window. The support may be configured to decouple the transducer from the round window such that the transducer can be removed from the middle ear of the user, for example when the support is affixed to the middle ear. Removal of the transducer from the middle ear without damaging the round window can allow safe removal of the transducer, for example when the patient wishes to receive MRI imaging.

37 Claims, 15 Drawing Sheets

(56) References Cited

U.S. PATENT DOCUMENTS

| | | |
|---|---|---|
| 3,712,962 A | 1/1973 | Epley |
| 3,764,748 A * | 10/1973 | Branch ............... H04R 25/606 |
| | | 381/190 |
| 3,808,179 A | 4/1974 | Gaylord |
| 3,870,832 A | 3/1975 | Fredrickson |
| 3,882,285 A | 5/1975 | Nunley et al. |
| 3,985,977 A | 10/1976 | Beaty et al. |
| 4,002,897 A | 1/1977 | Kleinman et al. |
| 4,061,972 A | 12/1977 | Burgess |
| 4,075,042 A | 2/1978 | Das |
| 4,098,277 A | 7/1978 | Mendell |
| 4,109,116 A | 8/1978 | Victoreen |
| 4,120,570 A | 10/1978 | Gaylord |
| 4,207,441 A | 6/1980 | Chouard et al. |
| 4,248,899 A | 2/1981 | Lyon et al. |
| 4,252,440 A | 2/1981 | Frosch et al. |
| 4,281,419 A | 8/1981 | Treace |
| 4,303,772 A | 12/1981 | Novicky |
| 4,319,359 A | 3/1982 | Wolf |
| 4,334,315 A | 6/1982 | Ono et al. |
| 4,334,321 A | 6/1982 | Edelman |
| 4,339,954 A | 7/1982 | Anson et al. |
| 4,357,497 A | 11/1982 | Hochmair et al. |
| 4,380,689 A | 4/1983 | Giannetti |
| 4,428,377 A | 1/1984 | Zollner et al. |
| 4,524,294 A | 6/1985 | Brody |
| 4,540,761 A | 9/1985 | Kawamura et al. |
| 4,556,122 A | 12/1985 | Goode |
| 4,592,087 A | 5/1986 | Killion et al. |
| 4,606,329 A | 8/1986 | Hough |
| 4,611,598 A | 9/1986 | Hortmann et al. |
| 4,628,907 A | 12/1986 | Epley |
| 4,641,377 A | 2/1987 | Rush et al. |
| 4,654,554 A | 3/1987 | Kishi |
| 4,689,819 A | 8/1987 | Killion et al. |
| 4,696,287 A | 9/1987 | Hortmann et al. |
| 4,729,366 A | 3/1988 | Schaefer |
| 4,741,339 A | 5/1988 | Harrison et al. |
| 4,742,499 A | 5/1988 | Butler |
| 4,756,312 A | 7/1988 | Epley |
| 4,766,607 A | 8/1988 | Feldman |
| 4,774,933 A | 10/1988 | Hough et al. |
| 4,776,322 A | 10/1988 | Hough et al. |
| 4,782,818 A | 11/1988 | Mori |
| 4,800,884 A | 1/1989 | Heide et al. |
| 4,800,982 A | 1/1989 | Carlson |
| 4,817,607 A | 4/1989 | Tatge |
| 4,840,178 A | 6/1989 | Heide et al. |
| 4,845,755 A | 7/1989 | Busch et al. |
| 4,865,035 A | 9/1989 | Mori |
| 4,918,745 A | 4/1990 | Hutchison |
| 4,932,405 A | 6/1990 | Peeters et al. |
| 4,936,305 A | 6/1990 | Ashtiani et al. |
| 4,944,301 A | 7/1990 | Widin et al. |
| 4,948,855 A | 8/1990 | Novicky |
| 4,957,478 A | 9/1990 | Maniglia |
| 4,982,434 A | 1/1991 | Lenhardt et al. |
| 4,999,819 A | 3/1991 | Newnham et al. |
| 5,003,608 A | 3/1991 | Carlson |
| 5,012,520 A | 4/1991 | Steeger |
| 5,015,224 A | 5/1991 | Maniglia |
| 5,015,225 A | 5/1991 | Hough et al. |
| 5,031,219 A | 7/1991 | Ward et al. |
| 5,061,282 A | 10/1991 | Jacobs |
| 5,066,091 A | 11/1991 | Stoy et al. |
| 5,094,108 A | 3/1992 | Kim et al. |
| 5,117,461 A | 5/1992 | Moseley |
| 5,142,186 A | 8/1992 | Cross et al. |
| 5,163,957 A | 11/1992 | Sade et al. |
| 5,167,235 A | 12/1992 | Seacord et al. |
| 5,201,007 A | 4/1993 | Ward et al. |
| 5,259,032 A | 11/1993 | Perkins et al. |
| 5,272,757 A | 12/1993 | Scofield et al. |
| 5,276,910 A | 1/1994 | Buchele |
| 5,277,694 A | 1/1994 | Leysieffer et al. |
| 5,338,287 A | 8/1994 | Miller et al. |
| 5,360,388 A | 11/1994 | Spindel et al. |
| 5,378,933 A | 1/1995 | Pfannenmueller et al. |
| 5,402,496 A | 3/1995 | Soli et al. |
| 5,411,467 A | 5/1995 | Hortmann et al. |
| 5,425,104 A | 6/1995 | Shennib |
| 5,440,082 A | 8/1995 | Claes |
| 5,440,237 A | 8/1995 | Brown et al. |
| 5,455,994 A | 10/1995 | Termeer et al. |
| 5,456,654 A | 10/1995 | Ball |
| 5,531,787 A | 7/1996 | Lesinski et al. |
| 5,531,954 A | 7/1996 | Heide et al. |
| 5,535,282 A | 7/1996 | Luca |
| 5,554,096 A | 9/1996 | Ball |
| 5,558,618 A | 9/1996 | Maniglia |
| 5,571,148 A | 11/1996 | Loeb et al. |
| 5,572,594 A | 11/1996 | Devoe et al. |
| 5,606,621 A | 2/1997 | Reiter et al. |
| 5,624,376 A | 4/1997 | Ball et al. |
| 5,707,338 A | 1/1998 | Adams et al. |
| 5,715,321 A | 2/1998 | Andrea et al. |
| 5,721,783 A | 2/1998 | Anderson |
| 5,722,411 A | 3/1998 | Suzuki et al. |
| 5,729,077 A | 3/1998 | Newnham et al. |
| 5,740,258 A | 4/1998 | Goodwin-Johansson |
| 5,749,912 A | 5/1998 | Zhang et al. |
| 5,762,583 A | 6/1998 | Adams et al. |
| 5,772,575 A | 6/1998 | Lesinski et al. |
| 5,774,259 A | 6/1998 | Saitoh et al. |
| 5,782,744 A | 7/1998 | Money |
| 5,788,711 A | 8/1998 | Lehner et al. |
| 5,795,287 A | 8/1998 | Ball et al. |
| 5,797,834 A | 8/1998 | Goode |
| 5,800,336 A | 9/1998 | Ball et al. |
| 5,804,109 A | 9/1998 | Perkins |
| 5,804,907 A | 9/1998 | Park et al. |
| 5,814,095 A | 9/1998 | Muller et al. |
| 5,824,022 A | 10/1998 | Zilberman et al. |
| 5,825,122 A | 10/1998 | Givargizov et al. |
| 5,836,863 A | 11/1998 | Bushek et al. |
| 5,842,967 A | 12/1998 | Kroll |
| 5,851,199 A | 12/1998 | Peerless et al. |
| 5,857,958 A | 1/1999 | Ball et al. |
| 5,859,916 A | 1/1999 | Ball et al. |
| 5,879,283 A | 3/1999 | Adams et al. |
| 5,888,187 A | 3/1999 | Jaeger et al. |
| 5,897,486 A | 4/1999 | Ball et al. |
| 5,899,847 A | 5/1999 | Adams et al. |
| 5,900,274 A | 5/1999 | Chatterjee et al. |
| 5,906,635 A | 5/1999 | Maniglia |
| 5,913,815 A | 6/1999 | Ball et al. |
| 5,922,017 A | 7/1999 | Bredberg et al. |
| 5,922,077 A | 7/1999 | Espy et al. |
| 5,935,170 A | 8/1999 | Haakansson et al. |
| 5,940,519 A | 8/1999 | Kuo |
| 5,949,895 A | 9/1999 | Ball et al. |
| 5,984,859 A | 11/1999 | Lesinski |
| 5,987,146 A | 11/1999 | Pluvinage et al. |
| 6,001,129 A | 12/1999 | Bushek et al. |
| 6,005,955 A | 12/1999 | Kroll et al. |
| 6,024,717 A | 2/2000 | Ball et al. |
| 6,038,480 A | 3/2000 | Hrdlicka et al. |
| 6,045,528 A * | 4/2000 | Arenberg et al. ............... 604/28 |
| 6,050,933 A | 4/2000 | Bushek et al. |
| 6,068,589 A | 5/2000 | Neukermans |
| 6,068,590 A | 5/2000 | Brisken |
| 6,084,975 A | 7/2000 | Perkins |
| 6,093,144 A | 7/2000 | Jaeger et al. |
| 6,137,889 A * | 10/2000 | Shennib et al. ............... 381/328 |
| 6,139,488 A | 10/2000 | Ball |
| 6,153,966 A | 11/2000 | Neukermans |
| 6,174,278 B1 | 1/2001 | Jaeger et al. |
| 6,181,801 B1 | 1/2001 | Puthuff et al. |
| 6,190,305 B1 | 2/2001 | Ball et al. |
| 6,190,306 B1 | 2/2001 | Kennedy |
| 6,208,445 B1 | 3/2001 | Reime |
| 6,216,040 B1 | 4/2001 | Harrison |
| 6,217,508 B1 | 4/2001 | Ball et al. |
| 6,222,302 B1 | 4/2001 | Imada et al. |

(56) References Cited

U.S. PATENT DOCUMENTS

| | | |
|---|---|---|
| 6,222,927 B1 | 4/2001 | Feng et al. |
| 6,240,192 B1 | 5/2001 | Brennan et al. |
| 6,241,767 B1 | 6/2001 | Stennert et al. |
| 6,261,224 B1 | 7/2001 | Adams et al. |
| 6,277,148 B1 | 8/2001 | Dormer |
| 6,312,959 B1 | 11/2001 | Datskos |
| 6,339,648 B1 | 1/2002 | McIntosh et al. |
| 6,342,035 B1 | 1/2002 | Kroll et al. |
| 6,354,990 B1 | 3/2002 | Juneau et al. |
| 6,366,863 B1 | 4/2002 | Bye et al. |
| 6,374,143 B1 | 4/2002 | Berrang et al. |
| 6,385,363 B1 | 5/2002 | Rajic et al. |
| 6,387,039 B1 | 5/2002 | Moses |
| 6,390,971 B1 | 5/2002 | Adams et al. |
| 6,393,130 B1 | 5/2002 | Stonikas et al. |
| 6,422,991 B1 | 7/2002 | Jaeger |
| 6,432,248 B1 | 8/2002 | Popp et al. |
| 6,436,028 B1 * | 8/2002 | Dormer ............................ 600/25 |
| 6,438,244 B1 | 8/2002 | Juneau et al. |
| 6,445,799 B1 | 9/2002 | Taenzer et al. |
| 6,473,512 B1 | 10/2002 | Juneau et al. |
| 6,475,134 B1 | 11/2002 | Ball et al. |
| 6,491,622 B1 | 12/2002 | Kasic, II et al. |
| 6,491,644 B1 | 12/2002 | Vujanic et al. |
| 6,491,722 B1 | 12/2002 | Kroll et al. |
| 6,493,453 B1 | 12/2002 | Glendon |
| 6,493,454 B1 | 12/2002 | Loi et al. |
| 6,498,858 B2 | 12/2002 | Kates |
| 6,507,758 B1 | 1/2003 | Greenberg et al. |
| 6,519,376 B2 | 2/2003 | Biagi et al. |
| 6,536,530 B2 | 3/2003 | Schultz et al. |
| 6,537,200 B2 | 3/2003 | Leysieffer et al. |
| 6,547,715 B1 | 4/2003 | Mueller et al. |
| 6,549,633 B1 | 4/2003 | Westermann |
| 6,554,761 B1 | 4/2003 | Puria et al. |
| 6,575,894 B2 * | 6/2003 | Leysieffer et al. ............. 600/25 |
| 6,592,513 B1 | 7/2003 | Kroll et al. |
| 6,603,860 B1 | 8/2003 | Taenzer et al. |
| 6,620,110 B2 | 9/2003 | Schmid |
| 6,626,822 B1 | 9/2003 | Jaeger et al. |
| 6,629,922 B1 | 10/2003 | Puria et al. |
| 6,643,378 B2 | 11/2003 | Schumaier |
| 6,668,062 B1 | 12/2003 | Luo et al. |
| 6,676,592 B2 | 1/2004 | Ball et al. |
| 6,695,943 B2 | 2/2004 | Juneau et al. |
| 6,724,902 B1 | 4/2004 | Shennib et al. |
| 6,728,024 B2 | 4/2004 | Ribak |
| 6,735,318 B2 | 5/2004 | Cho |
| 6,754,358 B1 | 6/2004 | Boesen et al. |
| 6,754,537 B1 | 6/2004 | Harrison et al. |
| 6,801,629 B2 | 10/2004 | Brimhall et al. |
| 6,829,363 B2 | 12/2004 | Sacha |
| 6,842,647 B1 | 1/2005 | Griffith et al. |
| 6,888,949 B1 | 5/2005 | Vanden Berghe et al. |
| 6,900,926 B2 | 5/2005 | Ribak |
| 6,912,289 B2 | 6/2005 | Vonlanthen et al. |
| 6,920,340 B2 | 7/2005 | Laderman |
| 6,931,231 B1 | 8/2005 | Griffin |
| 6,940,989 B1 | 9/2005 | Shennib et al. |
| D512,979 S | 12/2005 | Corcoran et al. |
| 6,975,402 B2 | 12/2005 | Bisson et al. |
| 6,978,159 B2 | 12/2005 | Feng et al. |
| 7,024,010 B2 | 4/2006 | Saunders et al. |
| 7,043,037 B2 | 5/2006 | Lichtblau et al. |
| 7,050,675 B2 | 5/2006 | Zhou et al. |
| 7,057,256 B2 | 6/2006 | Mazur et al. |
| 7,058,182 B2 | 6/2006 | Kates |
| 7,072,475 B2 | 7/2006 | DeNap et al. |
| 7,076,076 B2 | 7/2006 | Bauman |
| 7,095,981 B1 | 8/2006 | Voroba et al. |
| 7,167,572 B1 | 1/2007 | Harrison et al. |
| 7,174,026 B2 | 2/2007 | Niederdrank et al. |
| 7,179,238 B2 * | 2/2007 | Hissong ............................ 601/46 |
| 7,203,331 B2 | 4/2007 | Boesen |
| 7,239,069 B2 | 7/2007 | Cho |
| 7,245,732 B2 | 7/2007 | Jorgensen et al. |
| 7,255,457 B2 | 8/2007 | Ducharme et al. |
| 7,289,639 B2 * | 10/2007 | Abel et al. .................... 381/312 |
| 7,322,930 B2 | 1/2008 | Jaeger et al. |
| 7,349,741 B2 | 3/2008 | Maltan et al. |
| 7,354,792 B2 | 4/2008 | Mazur et al. |
| 7,376,563 B2 | 5/2008 | Leysieffer et al. |
| 7,390,689 B2 | 6/2008 | Mazur et al. |
| 7,394,909 B1 | 7/2008 | Widmer et al. |
| 7,421,087 B2 | 9/2008 | Perkins et al. |
| 7,424,122 B2 | 9/2008 | Ryan |
| 7,444,877 B2 | 11/2008 | Li et al. |
| 7,547,275 B2 | 6/2009 | Cho et al. |
| 7,630,646 B2 | 12/2009 | Anderson et al. |
| 7,645,877 B2 | 1/2010 | Gmeiner et al. |
| 7,668,325 B2 | 2/2010 | Puria et al. |
| 7,867,160 B2 | 1/2011 | Pluvinage et al. |
| 7,883,535 B2 | 2/2011 | Cantin et al. |
| 7,983,435 B2 | 7/2011 | Moses |
| 8,116,494 B2 | 2/2012 | Rass |
| 8,157,730 B2 | 4/2012 | Leboeuf et al. |
| 8,204,786 B2 | 6/2012 | Leboeuf et al. |
| 8,251,903 B2 | 8/2012 | Leboeuf et al. |
| 8,320,982 B2 | 11/2012 | Leboeuf et al. |
| 8,401,214 B2 | 3/2013 | Perkins et al. |
| 8,512,242 B2 | 8/2013 | Leboeuf et al. |
| 8,545,383 B2 | 10/2013 | Wenzel et al. |
| 8,600,089 B2 | 12/2013 | Wenzel et al. |
| 8,647,270 B2 | 2/2014 | Leboeuf et al. |
| 8,652,040 B2 | 2/2014 | Leboeuf et al. |
| 8,700,111 B2 | 4/2014 | Leboeuf et al. |
| 8,702,607 B2 | 4/2014 | Leboeuf et al. |
| 8,715,153 B2 | 5/2014 | Puria et al. |
| 8,715,154 B2 | 5/2014 | Perkins et al. |
| 8,787,609 B2 | 7/2014 | Perkins et al. |
| 8,788,002 B2 | 7/2014 | Leboeuf et al. |
| 8,845,705 B2 | 9/2014 | Perkins et al. |
| 8,885,860 B2 | 11/2014 | Djalilian et al. |
| 8,886,269 B2 | 11/2014 | Leboeuf et al. |
| 8,888,701 B2 | 11/2014 | Leboeuf et al. |
| 8,923,941 B2 | 12/2014 | Leboeuf et al. |
| 8,929,965 B2 | 1/2015 | Leboeuf et al. |
| 8,929,966 B2 | 1/2015 | Leboeuf et al. |
| 8,934,952 B2 | 1/2015 | Leboeuf et al. |
| 8,942,776 B2 | 1/2015 | Leboeuf et al. |
| 8,961,415 B2 | 2/2015 | Leboeuf et al. |
| 8,986,187 B2 | 3/2015 | Perkins et al. |
| 8,989,830 B2 | 3/2015 | Leboeuf et al. |
| 9,044,180 B2 | 6/2015 | Leboeuf et al. |
| 9,055,379 B2 | 6/2015 | Puria et al. |
| 9,131,312 B2 | 9/2015 | Leboeuf et al. |
| 9,277,335 B2 | 3/2016 | Perkins et al. |
| 9,289,135 B2 | 3/2016 | Leboeuf et al. |
| 9,289,175 B2 | 3/2016 | Leboeuf et al. |
| 9,301,696 B2 | 4/2016 | Leboeuf et al. |
| 9,314,167 B2 | 4/2016 | Leboeuf et al. |
| 9,392,377 B2 | 7/2016 | Olsen et al. |
| 9,427,191 B2 | 8/2016 | Leboeuf et al. |
| 9,521,962 B2 | 12/2016 | Leboeuf |
| 9,538,921 B2 | 1/2017 | Leboeuf et al. |
| 9,750,462 B2 | 9/2017 | Leboeuf et al. |
| 9,788,785 B2 | 10/2017 | Leboeuf |
| 9,788,794 B2 | 10/2017 | Leboeuf et al. |
| 9,794,653 B2 | 10/2017 | Aumer et al. |
| 9,801,552 B2 | 10/2017 | Romesburg et al. |
| 9,808,204 B2 | 11/2017 | Leboeuf et al. |
| 2001/0003788 A1 | 6/2001 | Ball et al. |
| 2001/0027342 A1 | 10/2001 | Dormer |
| 2001/0029313 A1 | 10/2001 | Kennedy |
| 2001/0043708 A1 | 11/2001 | Brimhall |
| 2001/0053871 A1 | 12/2001 | Zilberman et al. |
| 2001/0055405 A1 | 12/2001 | Cho |
| 2002/0012438 A1 | 1/2002 | Leysieffer et al. |
| 2002/0029070 A1 | 3/2002 | Leysieffer et al. |
| 2002/0030871 A1 | 3/2002 | Anderson et al. |
| 2002/0035309 A1 | 3/2002 | Leysieffer |
| 2002/0086715 A1 | 7/2002 | Sahagen |
| 2002/0172350 A1 | 11/2002 | Edwards et al. |
| 2002/0183587 A1 | 12/2002 | Dormer |

(56) References Cited

U.S. PATENT DOCUMENTS

| | | |
|---|---|---|
| 2003/0064746 A1 | 4/2003 | Rader et al. |
| 2003/0097178 A1 | 5/2003 | Roberson et al. |
| 2003/0125602 A1 | 7/2003 | Sokolich et al. |
| 2003/0142841 A1 | 7/2003 | Wiegand |
| 2003/0208099 A1 | 11/2003 | Ball |
| 2003/0220536 A1* | 11/2003 | Hissong .................. 600/25 |
| 2004/0158157 A1 | 8/2004 | Jensen et al. |
| 2004/0165742 A1 | 8/2004 | Shennib et al. |
| 2004/0184732 A1 | 9/2004 | Zhou et al. |
| 2004/0208333 A1 | 10/2004 | Cheung et al. |
| 2004/0234089 A1 | 11/2004 | Rembrand et al. |
| 2004/0234092 A1 | 11/2004 | Wada et al. |
| 2004/0240691 A1 | 12/2004 | Grafenberg |
| 2005/0020873 A1 | 1/2005 | Berrang et al. |
| 2005/0036639 A1 | 2/2005 | Bachler et al. |
| 2005/0111683 A1 | 5/2005 | Chabries et al. |
| 2005/0163333 A1 | 7/2005 | Abel et al. |
| 2005/0226446 A1 | 10/2005 | Luo et al. |
| 2005/0267549 A1 | 12/2005 | Della Santina et al. |
| 2006/0023908 A1 | 2/2006 | Perkins et al. |
| 2006/0058573 A1 | 3/2006 | Neisz et al. |
| 2006/0062420 A1 | 3/2006 | Araki |
| 2006/0107744 A1 | 5/2006 | Li et al. |
| 2006/0129210 A1 | 6/2006 | Cantin et al. |
| 2006/0161227 A1 | 7/2006 | Walsh et al. |
| 2006/0161255 A1 | 7/2006 | Zarowski et al. |
| 2006/0177079 A1 | 8/2006 | Baekgaard Jensen et al. |
| 2006/0183965 A1 | 8/2006 | Kasic et al. |
| 2006/0189841 A1 | 8/2006 | Pluvinage et al. |
| 2006/0231914 A1 | 10/2006 | Carey, III |
| 2006/0233398 A1 | 10/2006 | Husung |
| 2006/0251278 A1 | 11/2006 | Puria et al. |
| 2006/0278245 A1* | 12/2006 | Gan ..................... 128/898 |
| 2007/0083078 A1 | 4/2007 | Easter et al. |
| 2007/0100197 A1 | 5/2007 | Perkins et al. |
| 2007/0127748 A1 | 6/2007 | Carlile et al. |
| 2007/0135870 A1 | 6/2007 | Shanks et al. |
| 2007/0161848 A1 | 7/2007 | Dalton et al. |
| 2007/0191673 A1 | 8/2007 | Ball et al. |
| 2007/0225776 A1 | 9/2007 | Fritsch et al. |
| 2007/0236704 A1 | 10/2007 | Carr et al. |
| 2007/0250119 A1 | 10/2007 | Tyler et al. |
| 2007/0251082 A1 | 11/2007 | Milojevic et al. |
| 2007/0286429 A1 | 12/2007 | Grafenberg et al. |
| 2008/0021518 A1 | 1/2008 | Hochmair et al. |
| 2008/0051623 A1 | 2/2008 | Schneider et al. |
| 2008/0077198 A1 | 3/2008 | Webb et al. |
| 2008/0107292 A1 | 5/2008 | Kornagel |
| 2008/0188707 A1 | 8/2008 | Bernard et al. |
| 2008/0298600 A1 | 12/2008 | Poe et al. |
| 2009/0023976 A1 | 1/2009 | Cho et al. |
| 2009/0043149 A1 | 2/2009 | Abel et al. |
| 2009/0092271 A1 | 4/2009 | Fay et al. |
| 2009/0097681 A1 | 4/2009 | Puria et al. |
| 2009/0131742 A1 | 5/2009 | Cho et al. |
| 2009/0141919 A1 | 6/2009 | Spitaels et al. |
| 2009/0157143 A1 | 6/2009 | Edler et al. |
| 2010/0034409 A1 | 2/2010 | Fay et al. |
| 2010/0048982 A1 | 2/2010 | Puria et al. |
| 2010/0114190 A1 | 5/2010 | Bendett et al. |
| 2010/0145135 A1 | 6/2010 | Ball et al. |
| 2010/0272299 A1 | 10/2010 | Van Schuylenbergh et al. |
| 2010/0312040 A1 | 12/2010 | Puria et al. |
| 2010/0317914 A1 | 12/2010 | Puria et al. |
| 2011/0125222 A1 | 5/2011 | Perkins et al. |
| 2011/0142274 A1 | 6/2011 | Perkins et al. |
| 2011/0144719 A1 | 6/2011 | Perkins et al. |
| 2011/0152601 A1 | 6/2011 | Puria et al. |
| 2011/0152603 A1 | 6/2011 | Perkins et al. |
| 2011/0152976 A1 | 6/2011 | Perkins et al. |
| 2013/0315428 A1 | 11/2013 | Perkins et al. |
| 2014/0275734 A1 | 9/2014 | Perkins et al. |
| 2014/0288358 A1 | 9/2014 | Puria et al. |
| 2015/0031941 A1 | 1/2015 | Perkins et al. |

FOREIGN PATENT DOCUMENTS

| | | |
|---|---|---|
| DE | 2044870 A1 | 3/1972 |
| DE | 3243850 A1 | 5/1984 |
| DE | 3508830 A1 | 9/1986 |
| EP | 0242038 A2 | 10/1987 |
| EP | 0291325 A2 | 11/1988 |
| EP | 0296092 A2 | 12/1988 |
| EP | 0242038 A3 | 5/1989 |
| EP | 0296092 A3 | 8/1989 |
| EP | 0352954 A2 | 1/1990 |
| EP | 0291325 A3 | 6/1990 |
| EP | 0352954 A3 | 8/1991 |
| EP | 1035753 A1 | 9/2000 |
| EP | 1435757 A1 | 7/2004 |
| EP | 1845919 A1 | 10/2007 |
| EP | 2272520 A1 | 1/2011 |
| FR | 2455820 A1 | 11/1980 |
| GB | 2085694 A | 4/1982 |
| JP | S60154800 A | 8/1985 |
| JP | S621726 B2 | 1/1987 |
| JP | S63252174 A | 10/1988 |
| JP | S6443252 A | 2/1989 |
| JP | H09327098 A | 12/1997 |
| JP | 2004193908 A | 7/2004 |
| JP | 2005516505 A | 6/2005 |
| JP | 2006060833 A | 3/2006 |
| KR | 100624445 B1 | 9/2006 |
| WO | WO-9209181 A1 | 5/1992 |
| WO | WO 97/36457 A1 | 10/1997 |
| WO | WO-9745074 A1 | 12/1997 |
| WO | WO-9806236 A1 | 2/1998 |
| WO | WO-9903146 A1 | 1/1999 |
| WO | WO-9915111 A1 | 4/1999 |
| WO | WO-0022875 A2 | 4/2000 |
| WO | WO-0022875 A3 | 7/2000 |
| WO | WO-0150815 A1 | 7/2001 |
| WO | WO-0158206 A2 | 8/2001 |
| WO | WO-0158206 A3 | 2/2002 |
| WO | WO-0239874 A2 | 5/2002 |
| WO | WO-0239874 A3 | 2/2003 |
| WO | WO-03030772 A2 | 4/2003 |
| WO | WO 03/063542 A2 | 7/2003 |
| WO | WO 03/063542 A3 | 1/2004 |
| WO | WO-2004010733 A1 | 1/2004 |
| WO | WO-2005015952 A1 | 2/2005 |
| WO | WO-2006039146 A2 | 4/2006 |
| WO | WO-2006042298 A2 | 4/2006 |
| WO | WO 2006/075169 A1 | 7/2006 |
| WO | WO 2006/075175 A1 | 7/2006 |
| WO | WO-2006071210 A1 | 7/2006 |
| WO | WO-2006042298 A3 | 12/2006 |
| WO | WO 2007/023164 * | 3/2007 |
| WO | WO-2009047370 A2 | 4/2009 |
| WO | WO-2009056167 A1 | 5/2009 |
| WO | WO-2009062142 A1 | 5/2009 |
| WO | WO-2009047370 A3 | 7/2009 |
| WO | WO-2009125903 A1 | 10/2009 |
| WO | WO-2010141895 A1 | 12/2010 |
| WO | WO-2010147935 A1 | 12/2010 |
| WO | WO-2010148324 A1 | 12/2010 |
| WO | WO-2010148345 A2 | 12/2010 |
| WO | WO-2010151629 A2 | 12/2010 |
| WO | WO-2010151636 A2 | 12/2010 |
| WO | WO-2010151647 A2 | 12/2010 |
| WO | WO-2011005479 A2 | 1/2011 |
| WO | WO-2011005500 A2 | 1/2011 |

OTHER PUBLICATIONS

Birch, et al. Microengineered systems for the hearing impaired. IEE Colloquium on Medical Applications of Microengineering, Jan. 31, 1996; pp. 2/1-2/5.

Gennum, GA3280 Preliminary Data Sheet: Voyageur TD Open Platform DSP System for Ultra Low Audio Processing, downloaded from the Internet: <<http://www.sounddesigntechnologies.com/products/pdf/37601DOC.pd>>, Oct. 2006; 17 pages.

(56) References Cited

OTHER PUBLICATIONS

International search report dated Jan. 28, 2011 for PCT/US2010/039445.

Lee, et al. The optimal magnetic force for a novel actuator coupled to the tympanic membrane: a finite element analysis. Biomedical engineering: applications, basis and communications. 2007; 19(3):171-177.

National Semiconductor, LM4673 Boomer: Filterless, 2.65W, Mono, Class D Audio Power Amplifier, [Data Sheet] downloaded from the Internet: <<http://www.national.com/ds/LM/LM4673.pdf>>; Nov. 1, 2007; 24 pages.

Puria et al. A gear in the middle ear. ARO Denver CO, 2007b.

Puria, et al. Middle Ear Morphometry From Cadaveric Temporal Bone MicroCT Imaging. Proceedings of the 4th International Symposium, Zurich, Switzerland, Jul. 27-30, 2006, Middle Ear Mechanics in Research and Otology, pp. 259-268.

Wang, et al. Preliminary Assessment of Remote Photoelectric Excitation of an Actuator for a Hearing Implant. Proceeding of the 2005 IEEE, Engineering in Medicine and Biology 27th nnual Conference, Shanghai, China. Sep. 1-4, 2005; 6233-6234.

Yi, et al. Piezoelectric Microspeaker with Compressive Nitride Diaphragm. The Fifteenth IEEE International Conference on Micro Electro Mechanical Systems, 2002; 260-263.

European search report and opinion dated Jun. 5, 2013 for EP Application No. 10797560.9.

Atasoy [Paper] Opto-acoustic Imaging. For BYM504E Biomedical Imaging Systems class at ITU, downloaded from the Internet www2.itu.edu.td-cilesiz/courses/BYM504- 2005-OA 504041413.pdf, 14 pages.

Athanassiou, et al. Laser controlled photomechanical actuation of photochromic polymers Microsystems. Rev. Adv. Mater. Sci. 2003; 5:245-251.

Baer, et al. Effects of Low Pass Filtering on the Intelligibility of Speech in Noise for People With and Without Dead Regions at High Frequencies. J. Acost. Soc. Am 112 (3), pt. 1, (Sep. 2002), pp. 1133-1144.

Best, et al. The influence of high frequencies on speech localization. Abstract 981 (Feb. 24, 2003) from www.aro.org/abstracts/abstracts.html.

Burkhard, et al. Anthropometric Manikin for Acoustic Research. J. Acoust. Soc. Am., vol. 58, No. 1, (Jul. 1975), pp. 214-222.

Camacho-Lopez, et al. Fast Liquid Crystal Elastomer Swims Into the Dark, Electronic Liquid Crystal Communications. Nov. 26, 2003; 9 pages total.

Carlile, et al. Spatialisation of talkers and the segregation of concurrent speech. Abstract 1264 (Feb. 24, 2004) from www.aro.org/abstracts/abstracts.html.

Cheng, et al. A Silicon Microspeaker for Hearing Instruments. Journal of Micromechanics and Microengineering 2004; 14(7):859-866.

Dictionary.com's (via American Heritage Medical Dictionary) online dictionary definition of 'percutaneous'. Accessed on Jun. 3, 2013. 2 pages.

Merriam-Webster's online dictionary definition of 'percutaneous'. Accessed on Jun. 3, 2013. 3 pages.

Datskos, et al. Photoinduced and thermal stress in silicon microcantilevers. Applied Physics Letters. Oct. 19, 1998; 73(16):2319-2321.

Decraemer, et al. A method for determining three-dimensional vibration in the ear. Hearing Res., 77:19-37 (1994).

Ear. Retrieved from the Internet: http://wwwmgs.bionet.nsc.ru/mgs/gnw/trrd/thesaurus/Se/ear.html. Accessed Jun. 17, 2008.

European search report and search opinion dated Oct. 24, 2012 for EP Application No. 10797545.0.

European search report and search opinion dated Nov. 5, 2013 for EP Application No. 10790292.

Fay. Cat eardrum mechanics. Ph.D. thesis. Dissertation submitted to Department of Aeronautics and Astronautics. Standford University. May 2001; 210 pages total.

Fay, et al. Cat eardrum response mechanics. Calladine Festschrift (2002), Ed. S. Pellegrino, The Netherlands, Kluwer Academic Publishers.

Fletcher. Effects of Distortion on the Individual Speech Sounds. Chapter 18, ASA Edition of Speech and Hearing in Communication, Acoust Soc.of Am. (republished in 1995) pp. 415-423.

Freyman, et al. Spatial Release from Informational Masking in Speech Recognition. J. Acost. Soc. Am., vol. 109, No. 5, pt. 1, (May 2001); 2112-2122.

Freyman, et al. The Role of Perceived Spatial Separation in the Unmasking of Speech. J. Acoust. Soc. Am., vol. 106, No. 6, (Dec. 1999); 3578-3588.

Gobin, et al. Comments on the physical basis of the active materials concept. Proc. SPIE 2003; 4512:84-92.

Hakansson, et al. Percutaneous vs. transcutaneous transducers for hearing by direct bone conduction (Abstract). Otolaryngol Head Neck Surg. Apr. 1990;102(4):339-44.

Hato, et al. Three-dimensional stapes footplate motion in human temporal bones. Audiol. Neurootol., 8:140-152 (Jan. 30, 2003).

Hofman, et al. Relearning Sound Localization With New Ears. Nature Neuroscience, vol. 1, No. 5, (Sep. 1998); 417-421.

International search report and written opinion dated Jan. 18, 2011 for PCT/US2010/039240.

International search report and written opinion dated Jan. 28, 2011 for PCT/US2010/039347.

International search report and written opinion dated Aug. 27, 2010 for PCT/US2011/038602.

International search report and written opinion dated Sep. 28, 2010 for PCT/US2010/039209.

International search report and written opinion dated Oct. 29, 2010 for PCT/US2010/037509.

International search report dated Mar. 29, 2011 for PCT/US2010/039776.

Izzo, et al. Laser Stimulation of Auditory Neurons: Effect of Shorter Pulse Duration and Penetration Depth. Biophys J. Apr. 15, 2008;94(8):3159-3166.

Izzo, et al. Laser Stimulation of the Auditory Nerve. Lasers Surg Med. Sep. 2006;38(8):745-753.

Izzo, et al. Selectivity of Neural Stimulation in the Auditory System: A Comparison of Optic and Electric Stimuli. J Biomed Opt. Mar.-Apr. 2007;12(2):021008.

Jin, et al. Speech Localization. J. Audio Eng. Soc. convention paper, presented at the AES 112th Convention, Munich, Germany, May 10-13, 2002, 13 pages total.

Killion. Myths About Hearing Noise and Directional Microphones. The Hearing Review. Feb. 2004; 11(2):14, 16, 18, 19, 72 & 73.

Killion. SNR loss: I can hear what people say but I can't understand them. The Hearing Review, 1997; 4(12):8-14.

Lee, et al. A Novel Opto-Electromagnetic Actuator Coupled to the tympanic Membrane. J Biomech. Dec. 5, 2008;41(16):3515-8. Epub Nov. 7, 2008.

Lezal. Chalcogenide glasses—survey and progress. Journal of Optoelectronics and Advanced Materials. Mar. 2003; 5(1):23-34.

Mah. Fundamentals of photovoltaic materials. National Solar Power Research Institute. Dec. 21, 1998, 3-9.

Markoff. Intuition + Money: An Aha Moment. New York Times Oct. 11, 2008, p. BU4, 3 pages total.

Martin, et al. Utility of Monaural Spectral Cues is Enhanced in the Presence of Cues to Sound-Source Lateral Angle. JARO. 2004; 5:80-89.

Moore. Loudness perception and intensity resolution. Cochlear Hearing Loss, Chapter 4, pp. 90-115, Whurr Publishers Ltd., London (1998).

Murugasu, et al. Malleus-to-footplate versus malleus-to-stapes-head ossicular reconstruction prostheses: temporal bone pressure gain measurements and clinical audiological data. Otol Neurotol. Jul. 2005; 2694):572-582.

Musicant, et al. Direction-Dependent Spectral Properties of Cat External Ear: New Data and Cross-Species Comparisons. J. Acostic. Soc. Am, May 10-13, 2002, vol. 87, No. 2, (Feb. 1990), pp. 757-781.

"Notice of allowance dated Jan. 28, 2013 for U.S. Appl. No. 12/818,449."

(56) References Cited

OTHER PUBLICATIONS

"Notice of allowance dated Mar. 27, 2015 for U.S. Appl. No. 12/794,969."
Notice of allowance dated Apr. 7, 2014 for U.S. Appl. No. 13/770,106.
Notice of allowance dated Jul. 2, 2014 for U.S. Appl. No. 12/822,810.
Notice of allowance dated Dec. 21, 2012 for U.S. Appl. No. 12/818,449.
O'Connor, et al. Middle ear Cavity and Ear Canal Pressure-Driven Stapes Velocity Responses in Human Cadaveric Temporal Bones. J Acoust Soc Am. Sep. 2006;120(3):1517-28.
"Office action dated Jan. 16, 2015 for U.S. Appl. No. 12/814,998."
"Office action dated Jan. 29, 2013 for U.S. Appl. No. 12/794,969."
Office action dated Feb. 25, 2013 for U.S. Appl. No. 12/822,810.
"Office action dated Mar. 3, 2015 for U.S. Appl. No. 14/219,180."
"Office action dated Apr. 10, 2015 for U.S. Appl. No. 14/300,441."
"Office action dated Apr. 25, 2014 for U.S. Appl. No. 12/794,969."
"Office action dated May 22, 2014 for U.S. Appl. No. 12/814,998."
Office action dated Jul. 2, 2013 for U.S. Appl. No. 12/818,434.
Office action dated Jul. 30, 2014 for U.S. Appl. No. 12/818,434.
"Office action dated Jul. 31, 2013 for U.S. Appl. No. 12/814,998."
Office action dated Aug. 3, 2012 for U.S. Appl. No. 12/822,810.
Office action dated Aug. 15, 2013 for U.S. Appl. No. 12/820,767.
"Office action dated Sep. 8, 2015 for U.S. Appl. No. 12/814,998."
"Office action dated Sep. 8, 2015 for U.S. Appl. No. 12/818,434."
Office action dated Sep. 12, 2013 for U.S. Appl. No. 12/822,810.
Office action dated Sep. 24, 2013 for U.S. Appl. No. 13/770,106.
"Office action dated Oct. 3, 2013 for U.S. Appl. No. 12/794,969."
Office action dated Oct. 23, 2012 for U.S. Appl. No. 12/818,434.
"Office action dated Nov. 3, 2014 for U.S. Appl. No. 12/794,969."
Office action dated Nov. 19, 2013 for U.S. Appl. No. 12/818,434.
Office action dated Nov. 23, 2012 for U.S. Appl. No. 12/820,767.
"Office action dated Dec. 18, 2012 for U.S. Appl. No. 12/814,998."
"Office action dated Dec. 19, 2014 for U.S. Appl. No. 12/818,434."
Perkins, et al. The EarLens System: New sound transduction methods. Hear Res. Feb. 2, 2010; 10 pages total.
Poosanaas, et al. Influence of sample thickness on the performance of photostrictive ceramics, J. App. Phys. Aug. 1, 1998; 84(3):1508-1512.
Puria, et al. Malleus-to-footplate ossicular reconstruction prosthesis positioning: cochleovestibular pressure optimization. Otol Nerotol. May 2005; 2693):368-379.
Puria, et al. Measurements and model of the cat middle ear: Evidence of tympanic membrane acoustic delay. J. Acoust. Soc. Am., 104(6):3463-3481 (Dec. 1998).
Puria, et al. Sound-Pressure Measurements in the Cochlear Vestibule of Human-Cadaver Ears. Journal of the Acoustical Society of America. 1997; 101 (5-1): 2754-2770.
Robles, et al. Mechanics of the mammalian cochlea. Physiol Rev. Jul. 2001;81(3):1305-52.
Roush. SiOnyx Brings "Black Silicon" into the Light; Material Could Upend Solar, Imaging Industries. Xconomy, Oct. 12, 2008, retrieved from the Internet: www.xconomy.com/boston/2008/10/12/sionyx-brings-black-silicon-into-the-light-material-could-upend-solar-imaging-industries 4 pages total.
Rubinstein. How Cochlear Implants Encode Speech, Curr Opin Otolaryngol Head Neck Surg. Oct. 2004;12(5):444-8; retrieved from the Internet: www.ohsu.edu/nod/documents/week3/Rubenstein.pdf.
Sekaric, et al. Nanomechanical resonant structures as tunable passive modulators. App. Phys. Lett. Nov 2003; 80(19):3617-3619.
Shaw. Transformation of Sound Pressure Level From the Free Field to the Eardrum in the Horizontal Plane. J. Acoust. Soc. Am., vol. 56, No. 6, (Dec. 1974), 1848-1861.
Shih. Shape and displacement control of beams with various boundary conditions via photostrictive optical actuators. Proc. IMECE. Nov. 2003; 1-10.
Sound Design Technologies,—Voyager TDTM Open Platform DSP System for Ultra Low Power Audio Processing—GA3280 Data Sheet. Oct. 2007; retrieved from the Internet: <<http://www.sounddes.com/pdf/37601DOC.pdf>>, 15 pages total.
Stenfelt, et al. Bone-Conducted Sound: Physiological and Clinical Aspects. Otology & Neurotology, Nov. 2005; 26 (6):1245-1261.
Stuchlik, et al. Micro-Nano Actuators Driven by Polarized Light. IEEE Proc. Sci. Meas. Techn. Mar. 2004; 151(2):131-136.
Suski, et al. Optically activated $ZnO/SiO2/Si$ cantilever beams. Sensors and Actuators A (Physical), 0 (nr: 24). 2003; 221-225.
Takagi, et al. Mechanochemical Synthesis of Piezoelectric PLZT Powder. KONA. 2003; 51(21):234-241.
Thakoor, et al. Optical microactuation in piezoceramics. Proc. SPIE. Jul. 1998; 3328:376-391.
Tzou, et al. Smart Materials, Precision Sensors/Actuators, Smart Structures, and Structronic Systems. Mechanics of Advanced Materials and Structures. 2004; 11:367-393.
Uchino, et al. Photostricitve actuators. Ferroelectrics. 2001; 258:147-158.
Vickers, et al. Effects of Low-Pass Filtering on the Intelligibility of Speech in Quiet for People With and Without Dead Regions at High Frequencies. J. Acoust. Soc. Am. Aug. 2001; 110(2):1164-1175.
Vinikman-Pinhasi, et al. Piezoelectric and Piezooptic Effects in Porous Silicon. Applied Physics Letters, Mar. 2006; 88(11): 11905-111906.
Web Books Publishing, "The Ear," accessed online Jan. 22, 2013, available online Nov. 2, 2007 at http://www.web-books.com/eLibrary/Medicine/Physiology/Ear/Ear.htm.
Wiener, et al. On the Sound Pressure Transformation by the Head and Auditory Meatus of the Cat. Acta Otolaryngol. Mar. 1966; 61(3):255-269.
Wightman, et al. Monaural Sound Localization Revisited. J Acoust Soc Am. Feb. 1997;101(2):1050-1063.
Yu, et al. Photomechanics: Directed bending of a polymer film by light. Nature. Sep. 2003; 425:145.
Fay, et al. Preliminary evaluation of a light-based contact hearing device for the hearing impaired. Otol Neurotol. Jul. 2013;34(5):912-21. doi: 10.1097/MAO.0b013e31827de4b1.
Fritsch, et al. EarLens transducer behavior in high-field strength MRI scanners. Otolaryngol Head Neck Surg. Mar. 2009;140(3):426-8. doi: 10.1016/j.otohns.2008.10.016.
Gantz, et al. Broad Spectrum Amplification with a Light Driven Hearing System. Combined Otolaryngology Spring Meetings, 2016 (Chicago).
Gantz, et al. Light Driven Hearing Aid: A Multi-Center Clinical Study. Association for Research in Otolaryngology Annual Meeting, 2016 (San Diego).
Gantz, et al. Light-Driven Contact Hearing Aid for Broad Spectrum Amplification: Safety and Effectiveness Pivotal Study. Otology & Neurotology Journal, 2016 (in review).
Headphones. Wikipedia Entry, downloaded from the Internet : en.wikipedia.org/wiki/Headphones. Accessed Oct. 27, 2008. 7 pages total.
Jian, et al. A 0.6 V, 1.66 mW energy harvester and audio driver for tympanic membrane transducer with wirelessly optical signal and power transfer. InCircuits and Systems (ISCAS), 2014 IEEE International Symposium on Jun. 1, 2014. 874-7. IEEE.
Khaleghi, et al. Characterization of Ear-Canal Feedback Pressure due to Umbo-Drive Forces: Finite-Element vs. Circuit Models. ARO Midwinter Meeting 2016, (San Diego).
Levy, et al. Characterization of the available feedback gain margin at two device microphone locations, in the fossa triangularis and Behind the Ear, for the light-based contact hearing device. Acoustical Society of America (ASA) meeting, 2013 (San Francisco).
Levy, et al. Extended High-Frequency Bandwidth Improves Speech Reception in the Presence of Spatially Separated Masking Speech. Ear Hear. Sep.-Oct. 2015;36(5):e214-24. doi: 10.1097/AUD.0000000000000161.
Moore, et al. Spectro-temporal characteristics of speech at high frequencies, and the potential for restoration of audibility to people with mild-to-moderate hearing loss. Ear Hear. Dec. 2008;29(6):907-22. doi: 10.1097/AUD.0b013e31818246f6.
Perkins, et al. Light-based Contact Hearing Device: Characterization of available Feedback Gain Margin at two device microphone locations. Presented at AAO-HNSF Annual Meeting, 2013 (Vancouver).

(56) References Cited

OTHER PUBLICATIONS

Perkins, et al. The EarLens Photonic Transducer: Extended bandwidth. Presented at AAO-HNSF Annual Meeting, 2011 (San Francisco).
Perkins, R. Earlens tympanic contact transducer: a new method of sound transduction to the human ear. Otolaryngol Head Neck Surg. Jun. 1996;114(6):720-8.
Puria, et al. Cues above 4 kilohertz can improve spatially separated speech recognition. The Journal of the Acoustical Society of America, 2011, 129, 2384.
Puria, et al. Extending bandwidth above 4 kHz improves speech understanding in the presence of masking speech. Association for Research in Otolaryngology Annual Meeting, 2012 (San Diego).
Puria, et al. Extending bandwidth provides the brain what it needs to improve hearing in noise. First international conference on cognitive hearing science for communication, 2011 (Linkoping, Sweden).
Puria, et al. Hearing Restoration: Improved Multi-talker Speech Understanding. 5th International Symposium on Middle Ear Mechanics in Research and Otology (MEMRO), Jun. 2009 (Stanford University).
Puria, et al. Imaging, Physiology and Biomechanics of the middle ear: Towards understating the functional consequences of anatomy. Stanford Mechanics and Computation Symposium, 2005, ed Fong J.
Puria, et al. Temporal-Bone Measurements of the Maximum Equivalent Pressure Output and Maximum Stable Gain of a Light-Driven Hearing System That Mechanically Stimulates the Umbo. Otol Neurotol. Feb. 2016;37(2):160-6. doi: 10.1097/MAO. 0000000000000941.
Puria, et al. The EarLens Photonic Hearing Aid. Association for Research in Otolaryngology Annual Meeting, 2012 (San Diego).
Puria, et al. The Effects of bandwidth and microphone location on understanding of masked speech by normal-hearing and hearing-impaired listeners. International Conference for Hearing Aid Research (IHCON) meeting, 2012 (Tahoe City).
Puria. Measurements of human middle ear forward and reverse acoustics: implications for otoacoustic emissions. J Acoust Soc Am. May 2003;113(5):2773-89.
Puria, S. Middle Ear Hearing Devices. Chapter 10. Part of the series Springer Handbook of Auditory Research pp. 273-308. Date: Feb. 9, 2013.
Song, et al. The development of a non-surgical direct drive hearing device with a wireless actuator coupled to the tympanic membrane. Applied Acoustics. Dec. 31, 2013;74(12):1511-8.
Dundas et al. The Earlens Light-Driven Hearing Aid: Top 10 questions and answers. Hearing Review. 2018;25(2):36-39.
Gantz, et al. Light-Driven Contact Hearing Aid for Broad-Spectrum Amplification: Safety and Effectiveness Pivotal Study. Otology & Neurotology. Copyright 2016. 7 pages.
Khaleghi, et al. Attenuating the ear canal feedback pressure of a laser-driven hearing aid. J Acoust Soc Am. Mar. 2017;141(3):1683.
Khaleghi et al. Attenuating the feedback pressure of a light-activated hearing device to allows microphone placement at the ear canal entrance. IHCON 2016, International Hearing Aid Research Conference, Tahoe City, CA, Aug. 2016.
Khaleghi et al. Mechano-Electro-Magnetic Finite Element Model of a Balanced Armature Transducer for a Contact Hearing Aid. Proc. MoH 2017, Mechanics of Hearing workshop, Brock University, Jun. 2017.
Khaleghi et al. Multiphysics Finite Element Model of a Balanced Armature Transducer used in a Contact Hearing Device. ARO 2017, 40th ARO MidWinter Meeting, Baltimore, MD, Feb. 2017.
Levy et al. Light-driven contact hearing aid: a removable direct-drive hearing device option for mild to severe sensorineural hearing impairment. Conference on Implantable Auditory Prostheses, Tahoe City, CA, Jul. 2017. 4 pages.
McElveen et al. Overcoming High-Frequency Limitations of Air Conduction Hearing Devices Using a Light-Driven Contact Hearing Aid. Poster presentation at The Triological Society, 120th Annual Meeting at COSM, Apr. 28, 2017; San Diego, CA.
Struck, et al. Comparison of Real-world Bandwidth in Hearing Aids vs Earlens Light-driven Hearing Aid System. The Hearing Review. TechTopic: EarLens. Hearingreview.com. Mar. 14, 2017. pp. 24-28.

* cited by examiner

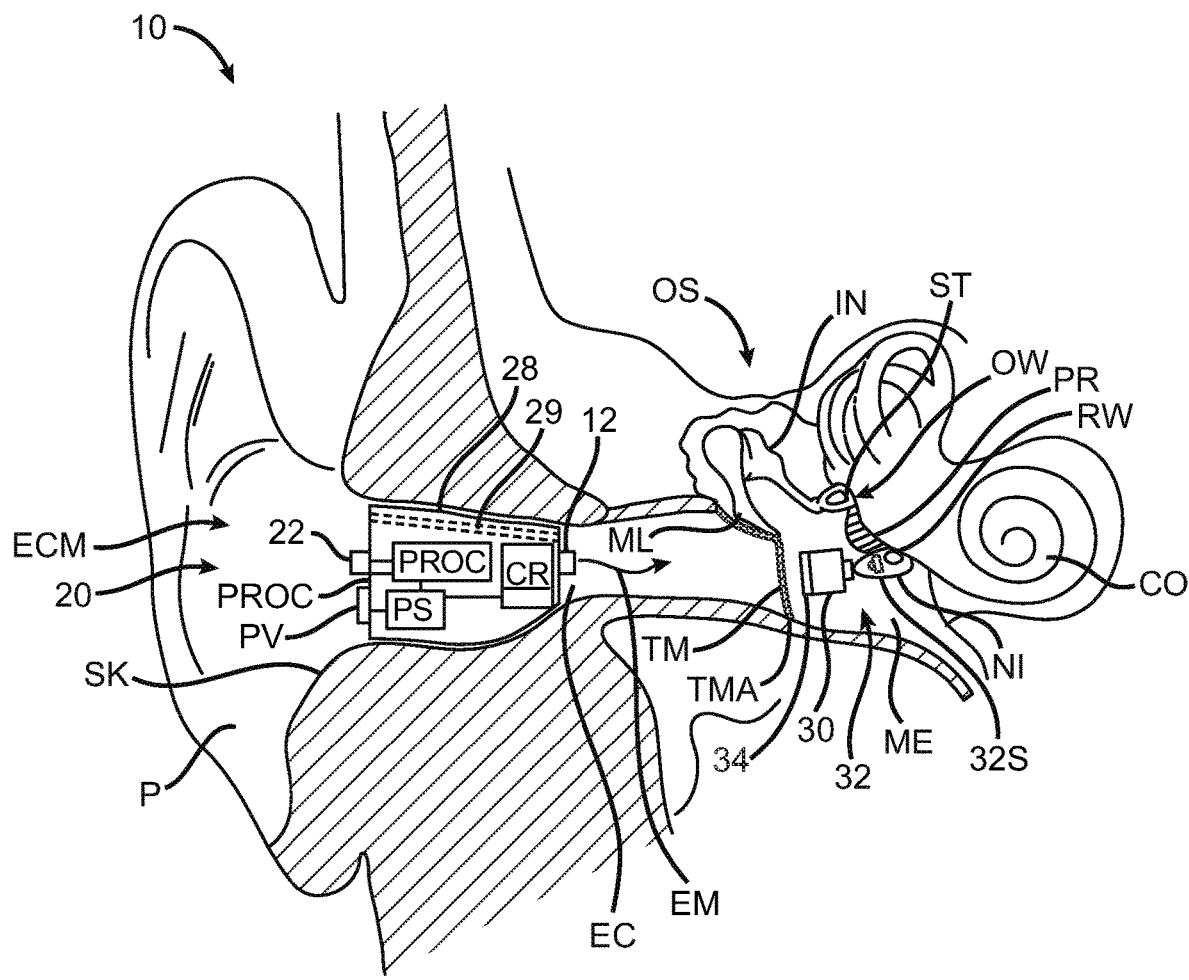
FIG. 1A1

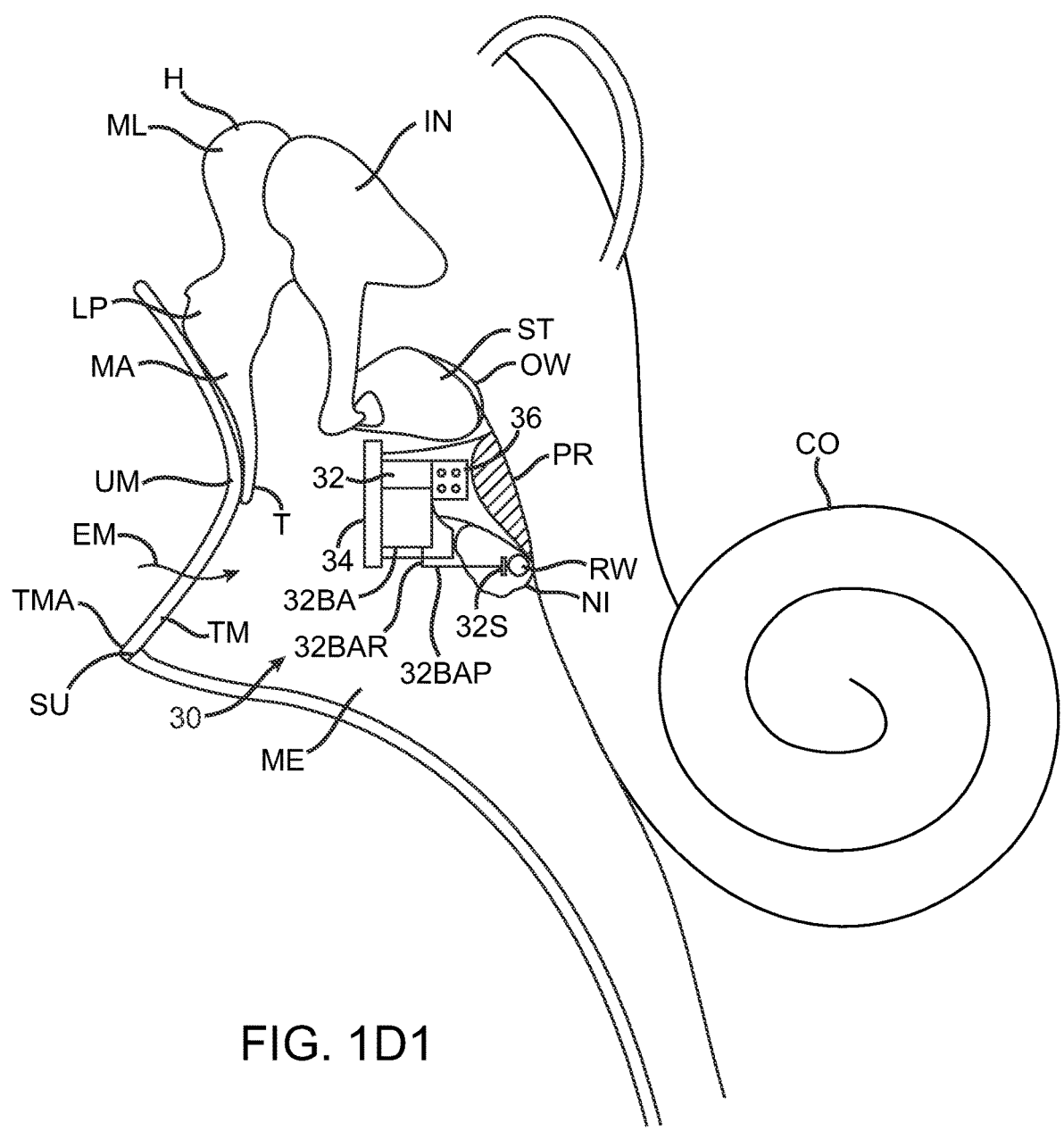
FIG. 1D1

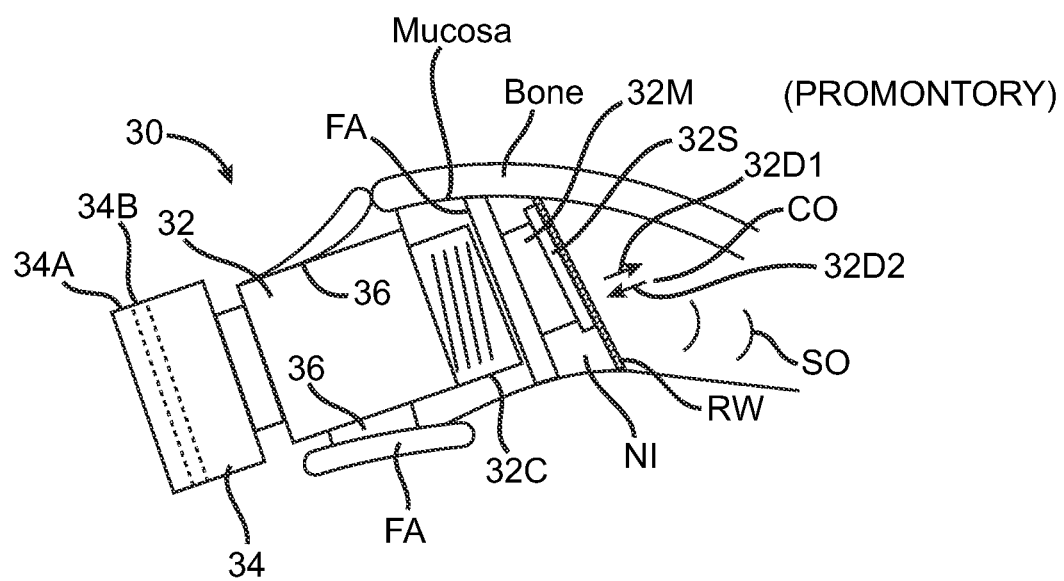
FIG. 1E1

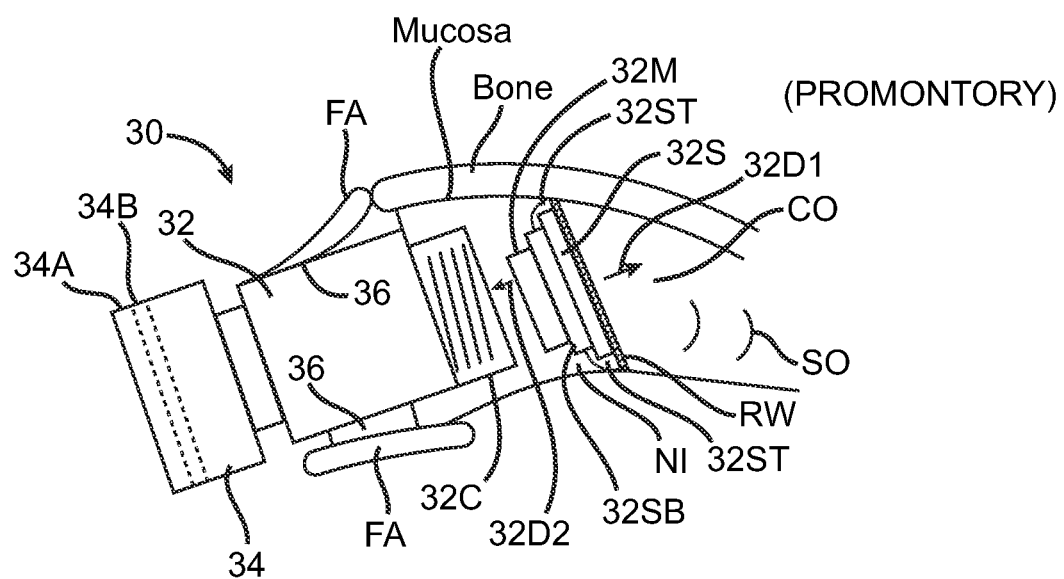
FIG. 1E2

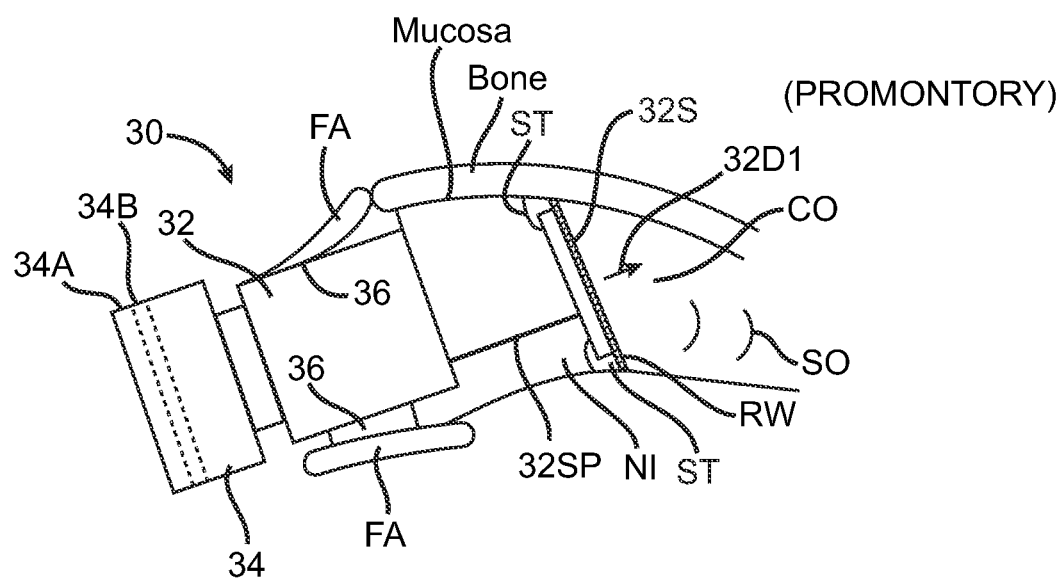
FIG. 1E3

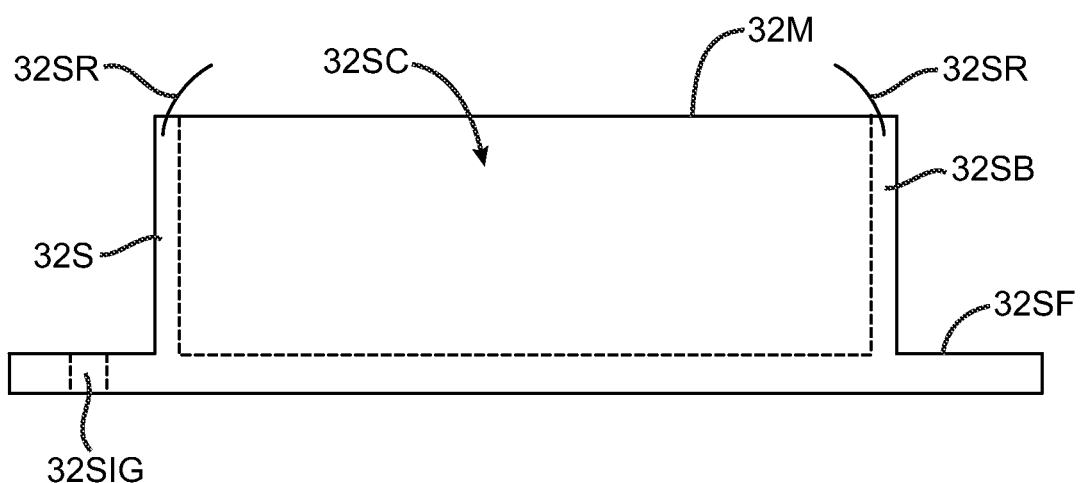
FIG. 1G1
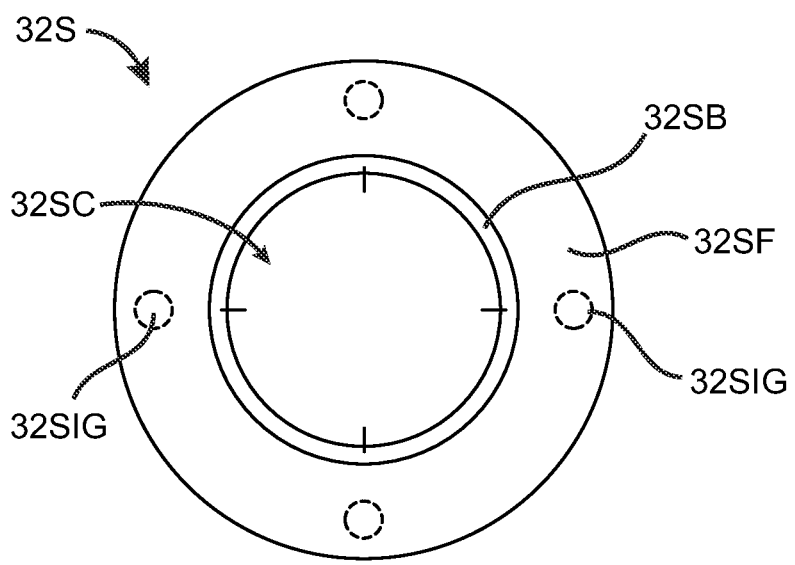
FIG. 1G2

FIG. 1G3

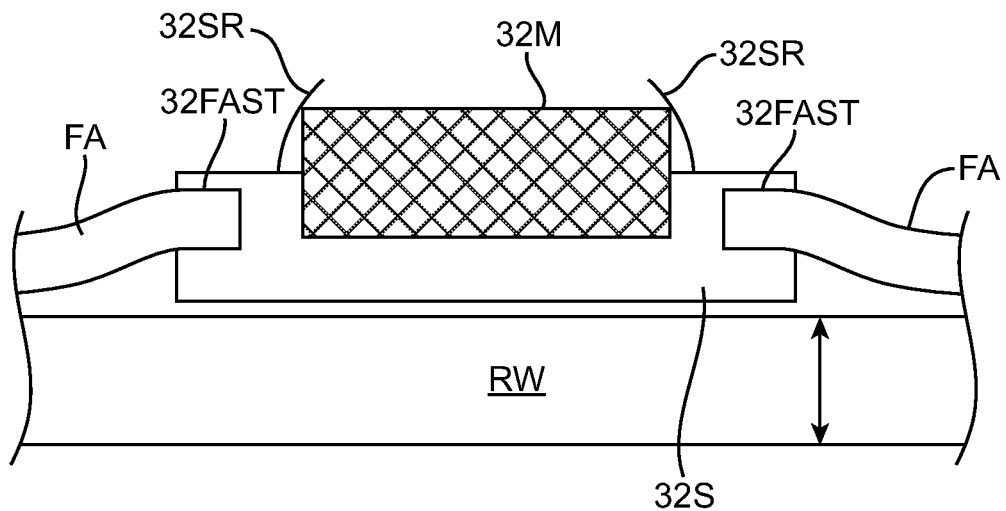
FIG. 1I1
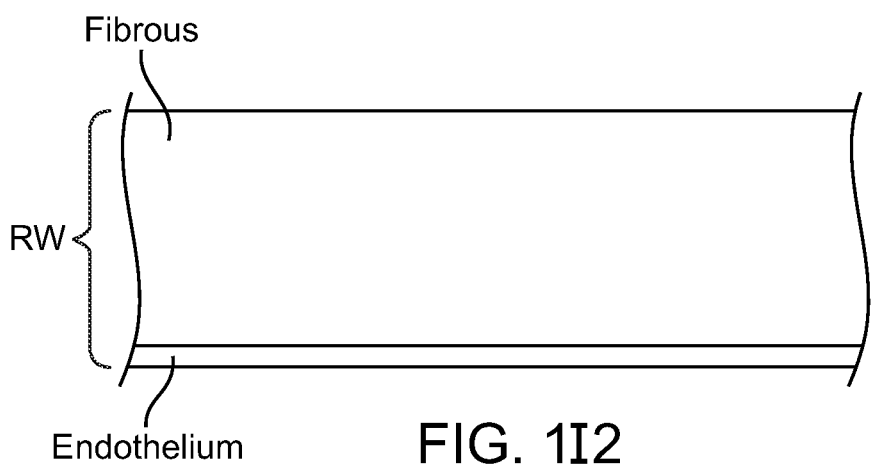
FIG. 1I2

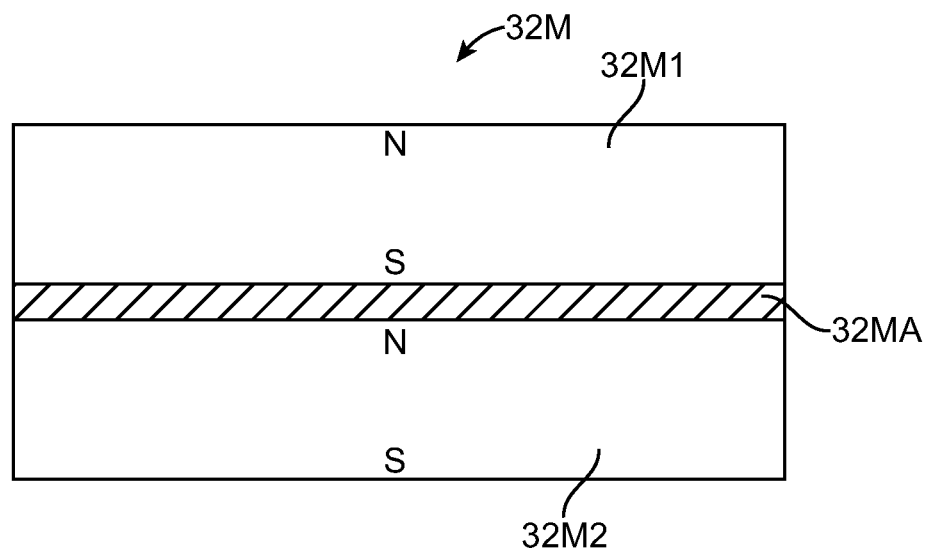
FIG. 1J
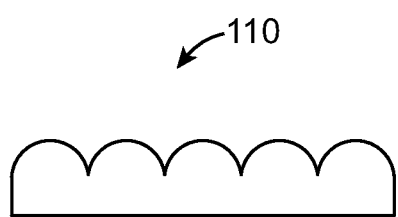 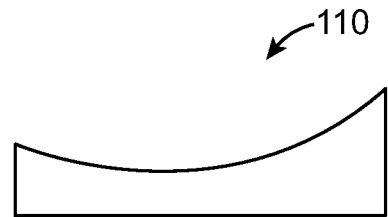
FIG. 1K　　　　　　　　FIG. 1L

ROUND WINDOW COUPLED HEARING SYSTEMS AND METHODS

CROSS-REFERENCES TO RELATED APPLICATIONS

The present application is a non-provisional of U.S. App. Ser. No. 61/219,286 filed 22 Jun. 2009, entitled "Round Window Coupled Hearing Systems and Methods", the full disclosure of which is incorporated herein by reference.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

1. Field of the Invention

The present invention is related to hearing systems, devices and methods. Although specific reference is made to hearing aid systems, embodiments of the present invention can be used in many applications in which a signal is used to stimulate the ear.

People like to hear. Hearing allows people to listen to and understand others. Natural hearing can include spatial cues that allow a user to hear a speaker, even when background noise is present. People also like to communicate with those who are far away, such as with cellular phones.

Hearing devices can be used with communication systems to help the hearing impaired and to help people communicate with others who are far away. Hearing impaired subjects need hearing aids to verbally communicate with those around them. Open canal hearing aids have proven to be successful in the marketplace because of increased comfort and an improved cosmetic appearance. Another reason why open canal hearing aides can be popular is reduced occlusion of the ear canal. Occlusion can result in an unnatural, tunnel-like hearing effect which can be caused by large hearing aids which block the ear canal. In at least some instances, occlusion be noticed by the user when he or she speaks and the occlusion results in an unnatural sound during speech. However, a problem that may occur with open canal hearing aids is feedback. The feedback may result from placement of the microphone in too close proximity with the speaker or the amplified sound being too great. Thus, feedback can limit the degree of sound amplification that a hearing aid can provide. Although feedback can be minimized by placing the microphone outside the ear canal, this placement can result in the device providing an unnatural sound that is devoid of the spatial location information cues present with natural hearing.

In some instances, feedback may be decreased by using non-acoustic means of stimulating the natural hearing transduction pathway, for example stimulating the tympanic membrane, bones of the ossicular chain and/or the cochlea. An output transducer may be placed on the eardrum, the ossicles in the middle ear, or the cochlea to stimulate the hearing pathway. However, surgery is often needed to place a hearing device on the ossicles or cochlea, and such surgery can involve delicate and complex movements to position the implant and can be somewhat invasive, for example with the cutting of bone, in at least some instances. At least some of the prior implants located on the ossicles or the cochlea can result in occlusion in at least some instances, and distortion of the sound can be perceptible in at least some instances.

Although it has been proposed to couple optically to a transducer placed on ossicles, in at least some instances the prior systems that transmit light to a transducer can result in perceptible noise and distortion in the optically transmitted signal, such that the sound quality of such devices can be less than ideal in at least some instances. For example, at least some optical systems may comprise non-linearity that can distort the signal and may result in user-perceptible distortion in at least some instances. Work in relation to embodiments of the present invention also suggests that vibration of a photodetector can result in distortion of the transmitted signal, for example when vibration affects optical coupling from a light source to the photodetector. Also, at least some of the proposed optically coupled devices have been affixed to vibratory structures of the ear, which can result in a user perceptible occlusion due to the mass of the device affixed to the vibratory structure of the ear.

Although coupling to the round window has been proposed, the round window is a thin and delicate membrane and safe coupling to the round window can be difficult to achieved to in at least some instances. For example, a permanent magnet securely fixed to the external surface of the round window of the cochlea can result in damage to the round window in at least some instances, for example when the round window is removed. Although a magnetic securely fixed to the round window may result in user perceived sound, in at least some instances a magnet positioned on the structures of the ear may be sensitive to external electromagnetic fields that can result in a perceptible noise. For example a humming sound may be perceived by the user in at least some instances. Also, it may be important for the patient to receive an imaging study at some point during his or her life, and removal of a magnet securely fixed to the round window can be difficult in at least some instances. A magnet securely fixed to the round window may damage the thin an sensitive tissue of the round window, such that cochlear fluid may leak from the round window and potentially damage the cochlea and permanently impair hearing in at least some instances.

2. Description of the Background Art

Patents and publications that may be relevant to the present application include: U.S. Pat. Nos. 3,585,416; 3,764,748; 3,882,285; 5,142,186; 5,360,388; 5,554,096; 5,624,376; 5,795,287; 5,800,336; 5,825,122; 5,857,958; 5,859,916; 5,888,187; 5,897,486; 5,913,815; 5,949,895; 6,005,955; 6,068,590; 6,093,144; 6,139,488; 6,174,278; 6,190,305; 6,208,445; 6,217,508; 6,222,302; 6,241,767; 6,422,991; 6,475,134; 6,519,376; 6,620,110; 6,626,822; 6,676,592; 6,728,024; 6,735,318; 6,900,926; 6,920,340; 7,072,475; 7,095,981; 7,239,069; 7,289,639; D512,979; 2002/0086715; 2003/0142841; 2004/0234092; 2005/0020873; 2006/0107744; 2006/0233398; 2006/075175; 2007/0083078; 2007/0191673; 2008/0021518; 2008/0107292; commonly owned U.S. Pat. Nos. 5,259,032; 5,276,910; 5,425,104; 5,804,109; 6,084,975; 6,554,761; 6,629,922; U.S. Publication Nos. 2006/0023908; 2006/0189841; 2006/0251278; and 2007/0100197. Non-U.S. patents and publications that may be relevant include EP1845919 PCT Publication Nos. WO 03/063542; WO 2006/075175; U.S. Publication Nos. Journal publications that may be relevant include: Ayatollahi et al., "Design and Modeling of Micromachines Condenser MEMS Loudspeaker using Permanent Magnet Neodymium-Iron-Boron (Nd—Fe—B)", ISCE, Kuala Lampur, 2006; Birch et al, "Microengineered Systems for the Hearing Impaired", IEE, London, 1996; Cheng et al., "A silicon microspeaker for hearing instruments", J. Micromech. Microeng., 14 (2004) 859-866; Yi et al., "Piezoelectric microspeaker with compressive nitride diaphragm", IEEE, 2006, and Zhigang Wang et al., "Preliminary Assessment of Remote Photoelectric Excitation of an Actuator for a Hearing Implant", IEEE Engineering in Medicine and Biology 27th Annual Conference, Shanghai, China, Sep. 1-4, 2005. Other publications of interest include: Gennum GA3280 Preliminary Data Sheet, "Voyager TDTM. Open Platform DSP System for Ultra Low Power Audio Processing" and National Semiconductor LM4673 Data Sheet, "LM4673 Filterless, 2.65 W, Mono, Class D audio Power Amplifier"; Puria, S. et al., Middle ear morphometry from cadaveric temporal bone micro CT imaging, Invited Talk. MEMRO 2006, Zurich; Puria, S. et al, A gear in the middle ear ARO 2007, Baltimore, Md.; and Lee et al., "The Optimal Magnetic Force For A Novel Actuator Coupled to the Tympanic Membrane: A Finite Element Analysis," Biomedical Engineering: Applications, Basis and Communications, Vol. 19, No. 3(171-177), 2007.

For the above reasons, it would be desirable to provide hearing systems which at least decrease, or even avoid, at least some of the above mentioned limitations of the prior hearing devices. For example, there is a need to provide a safe and comfortable hearing device which provides hearing with natural qualities, for example with spatial information cues, and which allow the user to hear with less occlusion, distortion and feedback than prior devices.

BRIEF SUMMARY OF THE INVENTION

Embodiments of the present invention provide improved hearing systems, devices and methods that overcome at least some of the limitations of the prior hearing devices. A support can be configured for placement in the middle ear to couple a transducer to the round window, such that the transducer can be removed from the round window without damaging the round window. The support can be configured to couple the transducer to the round window such that the support can be removed from the round window. Alternatively or in combination, the support may be configured to decouple the transducer from the round window such that the transducer can be removed from the middle ear of the user, for example when the support is affixed to the middle ear. Removal of the transducer from the middle ear without damaging the round window can allow safe removal of the transducer, for example when the patient wishes to receive MRI imaging. For example, the transducer may comprise a magnet coupled to the support to vibrate the round window in a first configuration of the support, and the magnet may be removed from the support with a second configuration of the support. The transducer in the middle ear can be configured to vibrate in response to electromagnetic energy in many ways. For example, a coil may be positioned in the ear canal to couple to the magnet. Alternatively, electromagnetic energy comprising light energy can be transmitted along the ear canal to the transducer in the middle ear to vibrate the transducer in response to light energy. For example, a photodetector can be positioned in the middle ear to drive the transducer, which may comprise a balance armature transducer coupled to the support, such that interference from magnetic fields is decreased.

In a first aspect, embodiments of the present invention provide a device to transmit sound to an ear of a user, in which the ear has a round window. The device comprises a support configured to couple to the round window, and a transducer configured to couple to the round window with the support to transmit the sound.

In many embodiments, the support is disposed at least partially between the transducer and the round window to inhibit contact of the transducer and round window.

In many embodiments, the support is configured to decouple from round window without tearing tissue of the round window.

Alternatively or in combination, the support can be configured to decouple from the transducer when the support is affixed to the round window. The support can be configured to affix to the round window, and the support can be configured to decouple from the transducer to remove the transducer from a middle ear of the user when the support is affixed to the round window. The support comprises a first side to couple to the round window and a second side opposite the first side to couple to the transducer.

In many embodiments, the support comprises an extension extending along the second side to inhibit tissue growth toward the transducer. The extension may extend along the second side substantially parallel to the first side. The extension may extend away from the first side along the transducer.

In many embodiments, the second side of the support comprises a recess sized to receive at least a portion of the transducer.

In many embodiments, the support comprises a structure configured to hold the transducer with a first configuration and release the transducer with a second configuration. The structure may comprise an extension configured to extend from the support to the transducer and decouple from the transducer to release the transducer.

In many embodiments, the transducer comprises at least one of a magnet, a coil, the coil and the magnet, a piezoelectric transducer, a photostrictive transducer, a balanced armature transducer or a magnetostrictive transducer. For example, the transducer may comprise the magnet and wherein the magnet is coupled to the support. The support may comprise a first side configured to couple to the round window and a second side configured to couple to the magnet. The support may comprise a first configuration with to couple to the magnet and a second configuration to release the magnet.

In many embodiments, the support comprises a soft biocompatible material configured to conform to the round window. The support may comprise a thin flexible material configured to deform with the round window in response to the sound.

In many embodiments, support is composed of a material comprising at least one of collagen, silicone, hydrogel, biocompatible plastic, or elastomer.

In many embodiments, the support is configured to couple to a mucosa, for example a mucosal tissue, disposed over the round window.

In many embodiments, the support is configured to the round window with a liquid. For example, the liquid comprises an oil.

In many embodiments, the support comprises a first side configured to couple to the round window and a second side configured to couple to the support. The support may comprise a first configuration to couple to the transducer and a second configuration to decouple from the transducer to remove the transducer from the middle ear.

In many embodiments, the transducer comprises the coil and the coil is configured for placement in an ear canal of the user to couple to the magnet.

In many embodiments, the transducer comprises the balanced armature transducer and a reed of the balanced armature tranducer is coupled to the support to vibrate the round window. A structure may extend from the reed to the support to couple the balanced armature transducer to the support in a first configuration. The structure extending from the reed to the support can be configured to decouple from at least the support in a second configuration to remove the balanced armature transducer from the middle ear of the user.

In another aspect, embodiments of the present invention provide a method of transmitting sound to an ear of a user, the ear having a round window, the method comprising: transmitting an electromagnetic signal to a transducer coupled to a support, wherein the transducer vibrates the round window with the support.

In another aspect, embodiments of the present invention provide a method of providing a hearing prosthesis to transmit sound to an ear of a user, in which the ear has a round window. A support and a transducer are provided. The support is coupled with the round window of the ear such that the transducer is coupled to the round window with the support to transmit the sound.

In many embodiments, the transducer contacts the support and the support is configured to separate from the transducer. The support may comprise a non-magnetic material.

In another aspect, embodiments of the present invention provide a device to transmit a sound to a user. The device comprises a transducer means for vibrating a round window of the user and a support means for coupling the transducer means to the round window.

BRIEF DESCRIPTION OF THE DRAWINGS

FIG. 1A1 shows a hearing system comprising an ear canal module and a transducer coupled to a round window of a user with a support, in accordance with embodiments of the present invention;

FIG. 1D1 shows an output transducer assembly comprising a balanced armature transducer coupled to the round window;

FIG. 1E1 shows a magnet and support coupled to the round window with fascia, in accordance with embodiments;

FIG. 1E2 shows a magnet and support coupled to the round window with the support affixed to the round window and the magnet coupled to the support and configured for removal;

FIG. 1E3 shows an transducer assembly coupled to the round window with a support and an extension such that the is transducer is configured to decouple from the support for removal of the transducer when the support is affixed to the round window;

FIGS. 1G1 and 1G2 show side and top views of the support with a first configuration to hold the magnet and barrier configured to inhibit tissue growth toward the magnet;

FIG. 1G3 shows the support as in FIGS. 1G1 and 1G2 with a second configuration configured to release the magnet;

FIG. 1I1 shows support configured to hold the magnet with a first configuration, barrier configured to inhibit tissue growth and an annular structure sized to receive fascia to hold the support in place over the round window in accordance with embodiments;

FIG. 1I2 shows tissue structure of the round window suitable for coupling in accordance with embodiments of the present invention;

FIG. 1J shows a magnet comprising a pair of opposing magnets, in accordance with embodiments;

FIG. 1K shows an optical coupler comprising at least one optic to couple to the light transmitted through the eardrum, in accordance with embodiments;

FIG. 1L shows the at least one optic of the coupler, in which the at least one optic comprises a lens, in accordance with embodiments; and FIG. 2 shows an experimental set up to determine optical transmission through the tympanic membrane, in accordance with embodiments.

DETAILED DESCRIPTION OF THE INVENTION

Embodiments as described herein can be used to transmit sound to a user. The sound may comprise sound from one or more sources such as a microphone, a cell phone, a Bluetooth connection, for example. In many embodiments, the sound is transmitted with a wireless signal through the eardrum such that the invasiveness of the surgery can be decreased. The wireless signal may comprise electromagnetic energy that is transmitted through the eardrum. The electromagnetic energy may comprise electromagnetic energy from a coil, for example. Alternatively or in combination, the electromagnetic energy may comprise light energy transmitted through the eardrum. The light energy my be transmitted through a posterior portion of the eardrum, for example through an inferior-posterior portion of the eardrum, so as to improve coupling efficiency of the light energy comprising the wireless sound signal transmitted through the eardrum.

As used herein light encompasses infrared light, visible light and ultraviolet light.

Figure 1A:
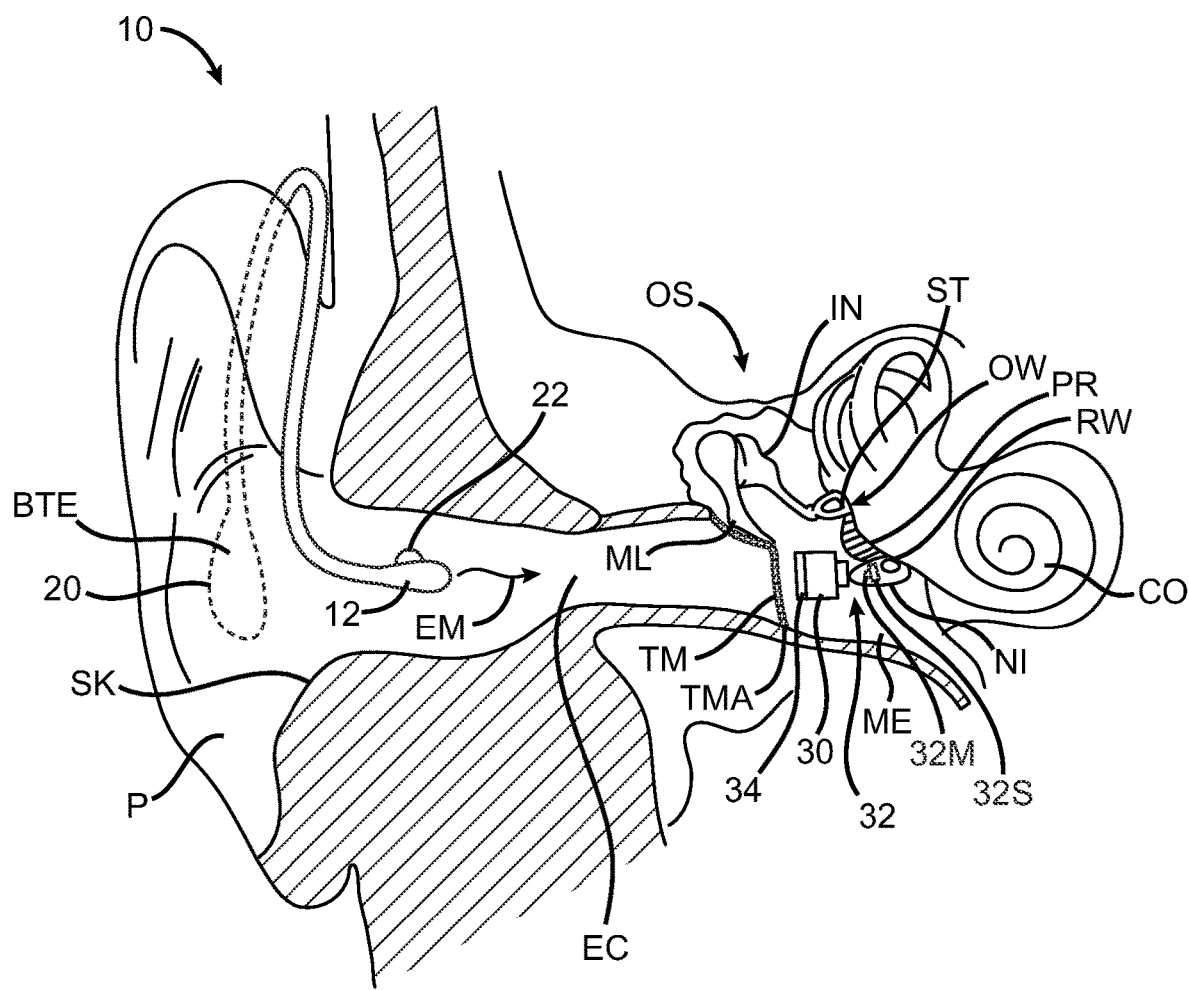
FIG. 1A shows an open canal hearing system comprising a BTE unit and a transducer coupled to a round window of a user with a support, in accordance with embodiments of the present invention.

FIG. 1A shows an open canal hearing system 10. The hearing system 10 comprises an input assembly 20 and an output assembly 30. The input assembly 20 may comprise a behind the ear (hereinafter "BTE") unit. The output assembly 30 comprises a transducer 32 coupled to a round window of a user with a support 32S.

The support 32S can be configured in many ways to couple the transducer to the round window. For example, the support 32S may comprise a soft biocompatible material sized for placement on the round window. The support 32S may be coupled to the round window RW with a liquid, for example an oil such as mineral oil, such that the support can be removed from the round window RW. The support may comprise many biocompatible materials, for example collagen, hydrogel, silicone, elastomer, silicone hydrogel. The support 32S can be configured to decouple from components transducer 32S, such transducer components can be separated from support 32S. For example support 32S may comprise a biocompatible materially configured to affix to the round window RW. The support 32S may comprise a first configuration configured to retain magnet 32M and second configuration configured to release magnet 32M to separate support 32S from magnet 32M. The support 32M may comprise a non-magnetic material such that the support 32S can remain affixed to the round window in the presence of strong magnetic fields, for example with magnetic resonance imaging.

The BTE unit can be configured in many ways. The BTE unit can be positioned behind a pinna P of the user, so as to decrease visibility of the BTE unit. The BTE unit can house electronics used to process and input signal. An input transducer of inputs assembly 10, for example microphone 22, is coupled to the BTE unit and can transmit an audio signal to the BTE unit. The BTE can convert the input signal into an electromagnetic signal EM. The electromagnetic signal may comprise an optical signal produced by at least one optical source such as a laser, or an electromagnetic signal from a coil. For example a support can extend into the ear canal and support a coil as described in as described in U.S. application Ser. No. 12/244,266, entitled, "Energy Delivery and Microphone Placement Methods for Improved Comfort in an Open Canal Hearing Aid", filed Oct. 2, 2008, the full disclosure of which is incorporated herein by reference and may be suitable for combination in accordance with embodiments of the present invention. Alternatively, the BTE unit can be coupled to an optical transmission structure 12 to emit an electromagnetic signal EM comprising the optical signal. The light transmission structure 12 can extend from the BTE into the ear canal EC. The light transmission structure 12 may support microphone 22. The light source may be housed in the BTE and coupled to the light transmission structure 12. Alternatively, the light source may be positioned in the ear canal, for example on a support disposed in the ear canal.

The input of input assembly 20 can come from many sources such as a microphone, a second microphone, or a radio coupled to an electronics devices such as a cell phone, computer, etc. Microphone 22 can be positioned in many locations, for example within the ear canal or near the ear canal opening to detect sound localization cues. The input transducer may comprise a second microphone positioned on the BTE unit for noise cancelation. The sound input to the assembly may comprise sound from a Bluetooth connection, and the BTE may comprise circuitry to couple with a cell phone, for example. For example, the input transducer assembly may be located substantially within the ear canal, as described in U.S. Pub. No. 2006/0251278, the full disclosure of which is incorporated by reference. The input transducer assembly may comprise a blue tooth connection to couple to a cell phone and my comprise, for example, components of the commercially available Sound ID 300, available from Sound ID of Palo Alto, Calif.

The output assembly 30 is configured for placement at least partially in the middle ear of the user. The output assembly 30 may comprise at least one detector 34 configured to receive electromagnetic energy EM comprising the optical signal $\lambda_S$. The output assembly comprise may comprise an output transducer, such that vibration of the transducer stimulates the cochlea in response to the optical signal. The output assembly 30 may comprise many kinds of transducers to vibrate the auditory system such that the user perceives sound. For example, the transducer may comprise at least one of a magnet, a coil, a coil and magnet transducer, a piezoelectric transducer, a balanced armature transducer, a photostrictive transducer or a magnetostrictive transducer.

The hearing system 10 can leave the natural hearing pathway of the user substantially function and intact with decreased interference from the system 10. Skin SK of the external ear can support the input assembly. The Pinna P can focus sound toward the ear canal EC, such that sound localization cues can be detected by microphone 22. The eardrum TM is coupled to ossicles OS so as to conduct sound to the cochlea CO where vibrations are sensed by the user as sound. The ossicles comprise a malleus ML, an incus IN and a stapes ST. The stapes ST couples to the cochlea with an oval window OW. The round window can be disposed along a channel of the cochlea opposite the oval window OW such that the round window RW vibrates in response to sound. The round window may be located in a round window niche NI. The eardrum TM may comprise an annulus TMA. An incision may be formed in the eardrum TM and optionally in the annulus TMA to insert components the output assembly in the middle ear ME.

In many embodiments, the at least one detector 34 comprises a photodetector, such as a photovoltaic diode, is positioned so as to receive light energy transmitted through a posterior portion of the eardrum TM, for example through an inferior/posterior portion of the eardrum, and the photodetector can be positioned within a range from about 0.5 mm to about 2 mm from the eardrum so as to couple efficiently with the light source. For example, the light source may be housed in the BTE and an optical fiber extending from the BTE to the ear canal transmits the light energy through the posterior portion of the eardrum to at least one detector.

FIG. 1A1 shows an input assembly 20 of system 10 comprising an ear canal module (hereinafter "ECM"). The ECM may comprise many of the components of the BTE unit and vice-versa. The ECM may be shaped from a mold of the user's ear canal EC. Circuitry (Circ.) can be coupled to microphone 22. The circuitry may comprise a sound processor. The ECM may comprise an energy storage device PS configured to store electrical energy. The storage device may comprise many known storage devices such at least one of a battery, a rechargeable batter, a capacitor, a supercapacitor, or electrochemical double layer capacitor (EDLC). The ECM can be removed, for example for recharging or when the user sleeps. The ECM may comprise a channel 29 to pass air so as to decrease occlusion. Although air is passed through channel 29, feedback can be decrease due to coupling of the transducer or electrode array directly to tissue.

The energy storage device PS may comprise a rechargeable energy storage device that can be recharged in many ways. For example, the energy storage device may be charged with a plug in connector coupled to a super capacitor for rapid charging. Alternatively, the energy storage device may be charged with an inductive coil or with a photodetector PV. The photodetector detector PV may be positioned on a proximal end of the ECM such that the photodetector is exposed to light entering the ear canal EC. The photodetector PV can be coupled to the energy storage device PS so as to charge the energy storage device PS. The photodetector may comprise many detectors, for example black silicone as described above. The rechargeable energy storage device can be provided merely for convenience, as the energy storage device PS may comprise batteries that the user can replace when the ECM is removed from ear canal.

The photodetector PV may comprise at least one photovoltaic material such as crystalline silicon, amorphous silicon, micromorphous silicon, black silicon, cadmium telluride, copper indium gallium selenide, and the like. In some embodiments, the photodetector PV may comprise black silicon, for example as described in U.S. Pat. Nos. 7,354,792 and 7,390,689 and available under from SiOnyx, Inc. of Beverly, Mass. The black silicon may comprise shallow junction photonics manufactured with semiconductor process that exploits atomic level alterations that occur in materials irradiated by high intensity lasers, such as a femto-second laser that exposes the target semiconductor to high intensity pulses as short as one billionth of a millionth of a second. Crystalline materials subject to these intense localized energy events may under go a transformative change, such that the atomic structure becomes instantaneously disordered and new compounds are "locked in" as the substrate re-crystallizes. When applied to silicon, the result can be a highly doped, optically opaque, shallow junction interface that is many times more sensitive to light than conventional semiconductor materials. Photovoltaic transducers for hearing devices are also described in detail in U.S. Patent Applications Nos. 61/073,271, entitled "Optical Electro-Mechanical Hearing Devices With Combined Power and Signal Architectures"; and 61/073,281, entitled "Optical Electro-Mechanical Hearing Devices with Separate Power and Signal", the full disclosures of which have been previously incorporated herein by reference and may be suitable for combination in accordance with some embodiments as described herein.

The output transducer assembly and anchor structure can be shaped in many ways to fit within the middle ear and affix to structures therein. For example, the transducer assembly may comprise a cross sectional size to pass through an incision in the eardrum TM and annulus TMA, such that bone that defines the ear canal can remain intact. The annulus TMA can be supported by a sulcus SU formed in the bony portion of the ear disposed between the external ear and middle ear. The eardrum can be incised along the annulus to form a flap of eardrum, a portion of which eardrum may remain connected to the user and placed on the margin of the ear canal when the transducer assembly 30 is positioned in the middle ear. Flap can be positioned after the transducer is positioned in the middle ear. The transducer assembly may comprise at least a portion shaped to fit within a round window niche. Alternatively or in combination, transducer assembly 30 may comprise a rounded concave portion 30R shaped to receive a rounded promontory of the middle ear.

The anchor structure can be configured to attach to many structures of the middle ear. For example, the anchor structure can be configured to affix to bone of the promontory. Alternatively or in combination, the anchor structure may be configured to couple to a bony lip near the round window. For example fascia may be affixed to the bony lip and support so as to hold the support over the round window.

The BTE may comprise many of the components of the ECM, for example photodetector PV, energy storage device PS, the processor and circuitry, as described above.

Figure 1B:
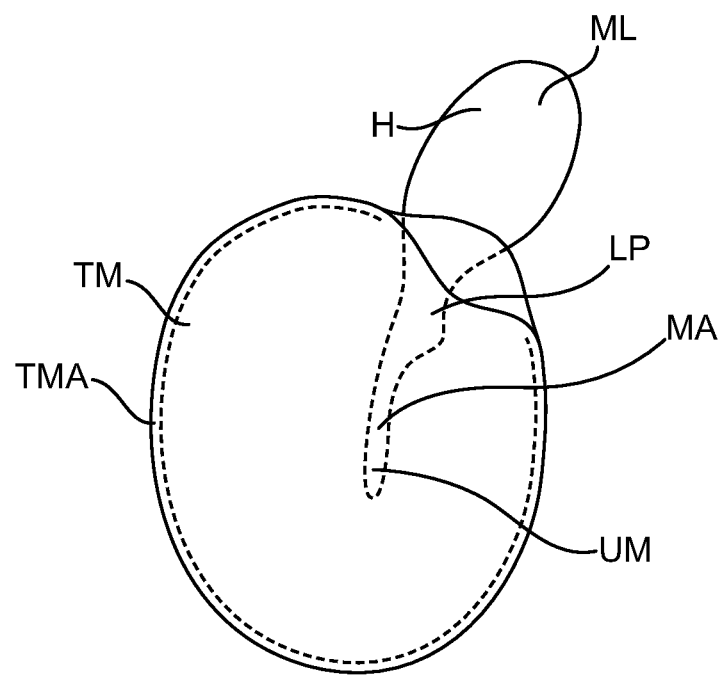
FIG. 1B shows the lateral side of the eardrum and FIG. 1C shows the medial side of the eardrum, suitable for incorporation of the hearing aid system of FIG. 1.
Figure 1C:
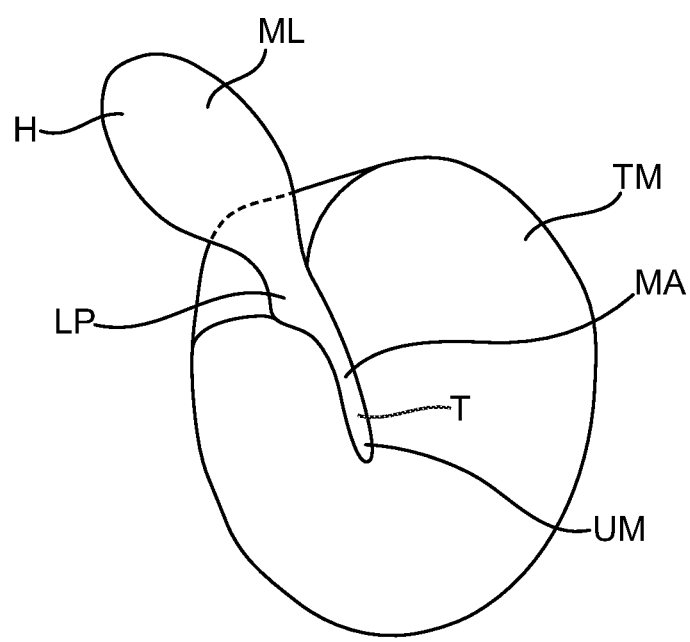

FIG. 1B shows the lateral side of the eardrum and FIG. 1C shows the medial side of the eardrum, suitable for incorporation of the hearing system of FIGS. 1A and 1A1. The eardrum TM is connected to a malleus ML. Malleus ML comprises a head H, a manubrium MA, a lateral process LP, and a tip T. Manubrium MA is disposed between head H and tip T and coupled to eardrum TM, such that the malleus ML vibrates with vibration of eardrum TM.

Figure 1D:
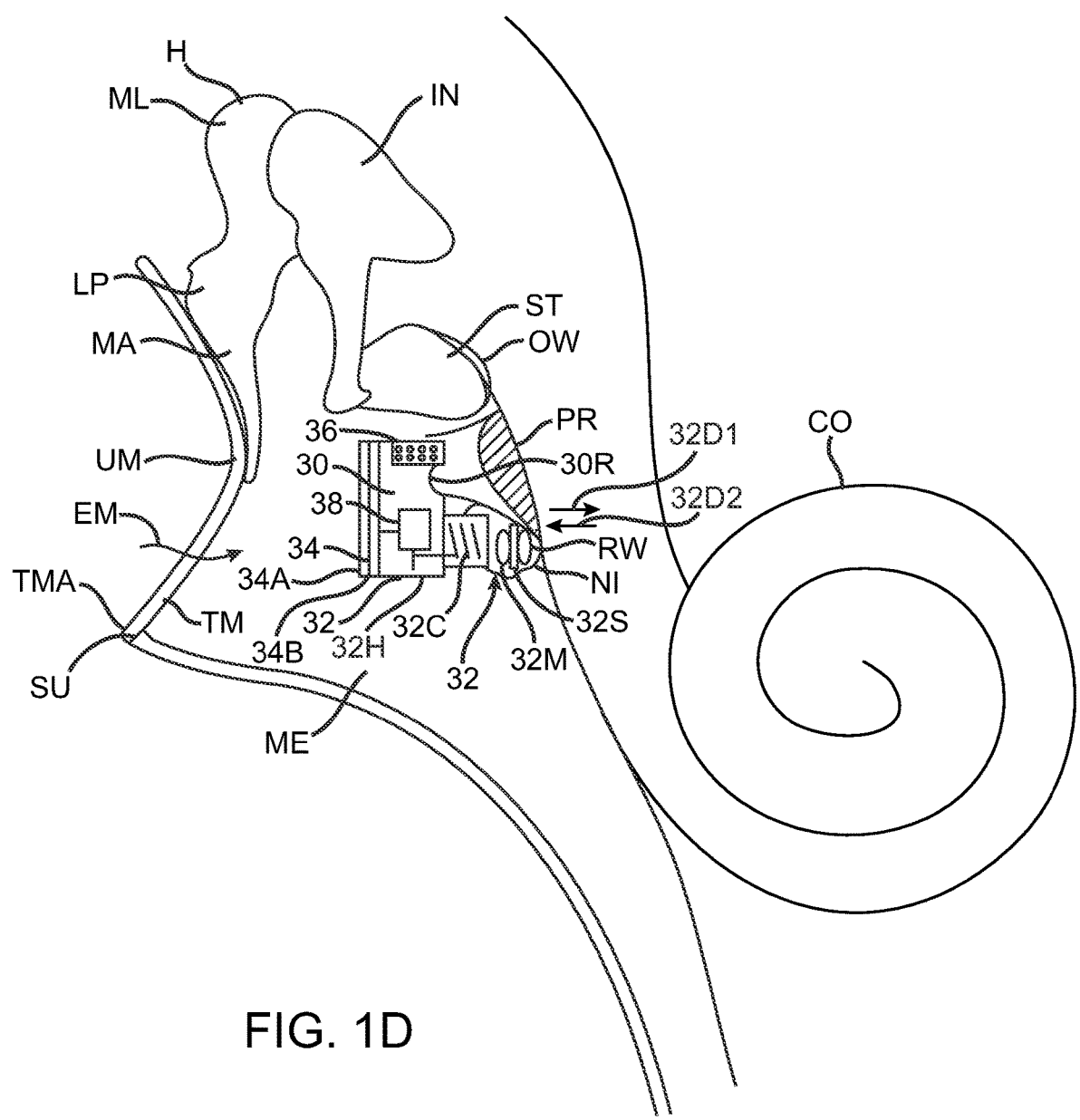
FIG. 1D shows an output transducer assembly comprising a photodetector coupled to a coil, in which the coil is sized to fit at least partially in the round window niche to couple to a magnet positioned on a support coupled to the round window.

FIG. 1D shows output transducer assembly 30 comprising at least one photodetector 34, an output transducer 32 and an anchor structure 36. The at least one photodetector 34 is coupled to an output transducer 32. The output transducer may comprise a coil 32C, in which the coil 32C is sized to fit at least partially in the round window niche NI so as to couple to magnet M positioned on support 32S coupled to the round window RW. The output transducer 34 may be coupled to the coil 3C with circuitry 38, such that the magnet vibrates to transmit sound in response to electromagnetic energy transmitted through eardrum TM. Output transducer assembly 30 may comprise an anchor structure 36 configured to affix the output transducer assembly to a substantially fixed structure of the ear, such as promontory PR. The anchor structure 36 may comprise a biocompatible structure configured to receive a tissue graft, for example, and may comprise at least one of a coating, a flange or holes for tissue integration. The anchor structure 36 can be affixed to tissue such that the location of the assembly remains substantially fixed when transducer 32 is coupled to the round window of the ear. The at least one detector 34, the circuitry 38 and the coil 32C may be hermetically sealed in a housing 32H, such that at least a portion of housing 32H comprising at least a portion of coil 32C is sized to fit at least partially within the round window niche NI to couple the coil 32C to the magnet 32M. The magnet 32M is sized to couple to the round window RW.

The at least one photodetector may be configured in many ways to vibrate the round window in response to electromagnetic energy EM comprising light energy. For example, the assembly 30 may comprise a first photodetector configured to receive a first at least one wavelength of light and a second photodetector configured to receive a second at least one wavelength of light, in which the coil is configured to urge the magnet in a first direction 32M1 to increase the pressure of the inner ear in response to the first at least one wavelength and to urge the magnet in a second direction 32M2 to decrease the pressure of inner ear in response to the second at least one wavelength. The first photodetector may transmit the second at least one wavelength of light such that the first photodetector can be positioned at least partially over the second photodetector to decrease the size of assembly 30. The first photodetector can be coupled to the sound transducer with a first polarity and the second photodetector coupled to the second photodetector with a second polarity, the first polarity opposite the second polarity. The first photodetector and the second photodetector may comprise at least one photovoltaic material such as crystalline silicon, amorphous silicon, micromorphous silicon, black silicon, cadmium telluride, copper indium gallium selenide, and the like. In some embodiments, the at least one of photodetector may comprise black silicon, for example as described in U.S. Pat. Nos. 7,354,792 and 7,390,689 and available under from SiOnyx, Inc. of Beverly, Mass. Alternatively or in combination, the assembly may comprise separated power and signal architectures, for example with the assembly comprising one photodetector. The first at least one wavelength of light and the second at least one wavelength of light may be pulse width modulated. Examples of circuitry and systems that can be configured to optically couple the implantable transducer assembly 30 with input transducer assembly 20 can be found in U.S. App. Nos. 61/073,271, filed Jun. 17, 2008, entitled "Optical Electro-Mechanical Hearing Devices With Combined Power and Signal Architectures"; 61/139,522, filed Dec. 19, 2008, entitled "Optical Electro-Mechanical Hearing Devices With Combined Power and Signal Architectures"; 61/139,522, filed May 11, 2009, entitled "Optical Electro-Mechanical Hearing Devices With Combined Power and Signal Architectures"; 61/073,281, filed Jun. 17, 2008, entitled "Optical Electro-Mechanical Hearing Devices with Separate Power and Signal"; 61/139,520, filed Dec. 19, 2008, entitled "Optical Electro-Mechanical Hearing Devices with Separate Power and Signal"; Ser. No. 12/486,100 filed Jun. 17, 2009, entitled "Optical Electro-Mechanical Hearing Devices With Combined Power and Signal Architectures"; Ser. No. 12/486,116 filed Jun. 17, 2009, entitled "Optical Electro-Mechanical Hearing Devices With Separate Power and Signal Components"; the full disclosures, all of which are incorporated by reference and suitable for combination in accordance with embodiments of the present invention.

In some embodiments, the photodetector 34 may comprise output transducer 32. For example the photodetector may comprise a photostrictive material configured to vibrate in response to light energy.

FIG. 1D1 shows output transducer assembly 30 comprising a balanced armature transducer 32BA coupled to the round window RW. The balanced armature transducer 32BA comprises a reed 32BAR. Reed 32BAR is coupled to the round window RW with an extension structure, for example a post 32BAP that extends from the reed toward the round window. The reed may be coupled with support 32S similar configured to couple the transducer to the round window. In some embodiments, the extension may comprise the support. The balanced armature transducer is configured to couple to the support in a first configuration. The balanced armature transducer is configured to decouple from the support in a second configuration, for example with decoupling of at least one of support 32S or post 32BAP from the transducer. For example, the reed may decouple from the post in the second configuration. Alternatively or in combination, the extension structure comprising the post may decouple from the support 32S.

Figure 1E:
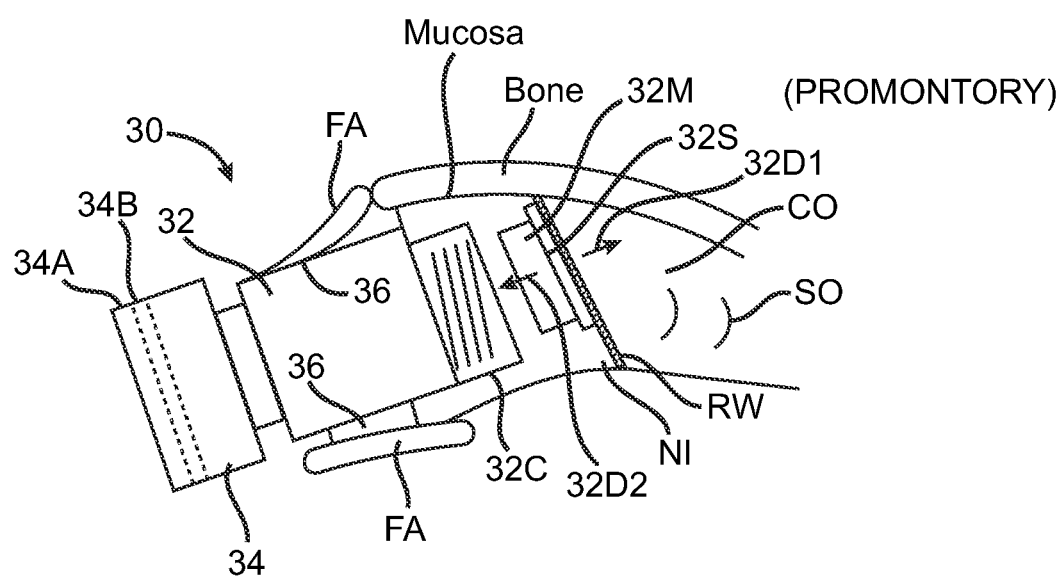
FIG. 1E shows an output transducer assembly coupled to the round window with fascia, in accordance with embodiments.

FIG. 1E shows output transducer assembly 30 coupled to the round window with fascia FA. The fascia FA can connect the transducer to the round window niche. The transducer assembly can be configured to extend at least partially within the round window to couple to the coil the magnet. The support may be releasably coupled to the round window, for example with an oil such as mineral oil disposed between the support and the round window to coat the support. Alternatively or in combination, the support may comprise a tissue growth inhibiting substance such that the support 32S does not become affixed to the round window, for example with tissue growth.

FIG. 1E1 shows a magnet and support coupled to the round window with fascia. The output transducer assembly may extend at least partially into the window and couple to surgically positioned fascia FA, such that the output transducer assembly is held in place. The magnet and support can be retained in position over the round window with fascia FA surgically positioned in the round window niche NI over the support 32S, magnet 32M, and round window RW such that the magnet and support are held in place. The support 32S can be configured to inhibit scarring as described above such that the support can be removed. Alternatively or in combination, the support can be configured to hold the magnet in a first configuration and release the magnet in a second configuration.

Figure 2:
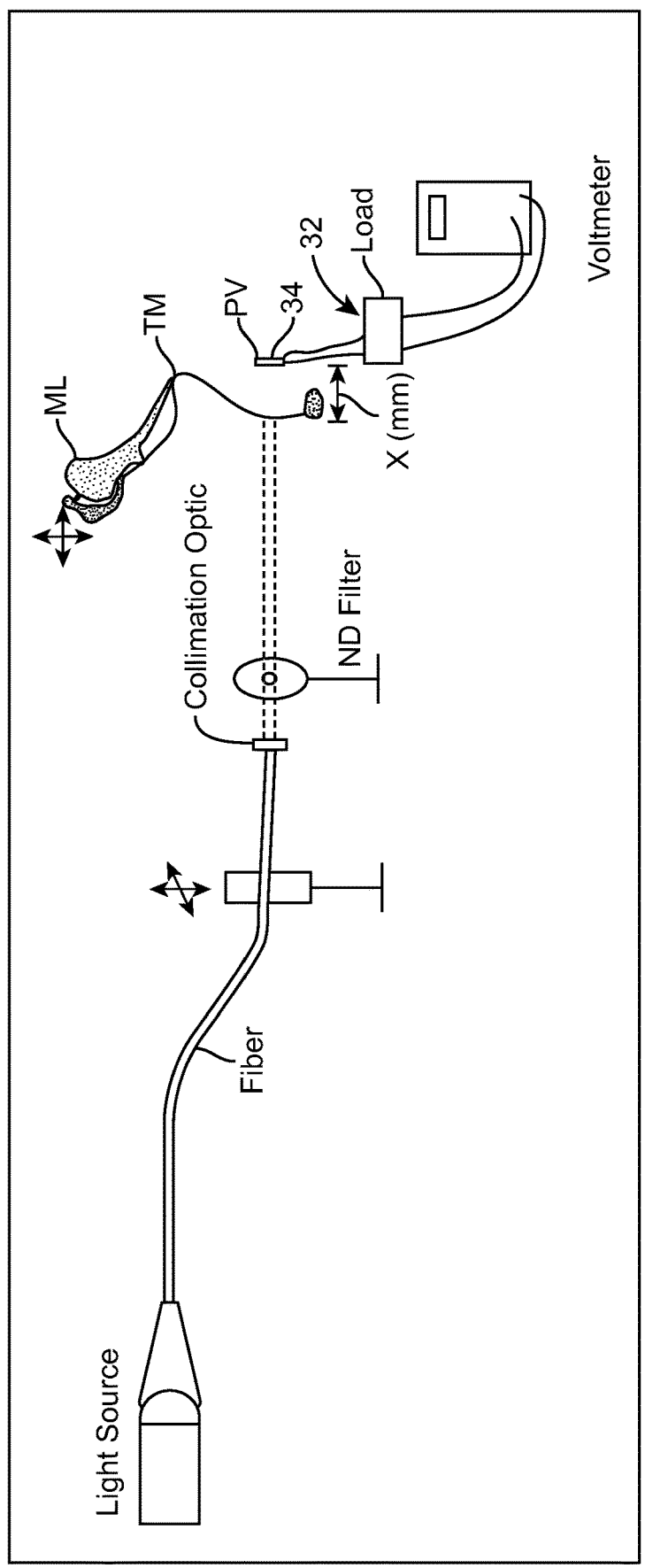

FIG. 1E2 shows a magnet and support coupled to the round window with the support affixed to the round window and the magnet coupled to the support and configured for removal. Work in relation to embodiments suggest that tissue can grow near the round window so as to connect to the support, and the support can be configured to release the magnet such that the support remains in place on the round window when the magnet is removed. For example, scar tissue ST may grow toward the support and at least partially cover the support, such that the support may be affixed to the round window. A person of ordinary skill in the art can conduct experimental studies to determine the growth and extent of scar tissue formation in response to the support and magnet, or other transducer coupling as described above. The support may comprise a first configuration configured to couple to the transducer and a second configuration configured to decouple from the transducer. The transducer can be removed from the middle ear of the user in the second configuration.

FIG. 1E3 shows an transducer assembly coupled to the round window with a support and an extension such that the transducer is configured to decoupled from the support for removal of the transducer when the support is affixed to the round window. The support is configured to contact the round window with a first side. The scar tissue may form along an outer portion of the support. The extension from the transducer to the support may be coupled to the support at an inner portion of the support, such that the extension and transducer can be decoupled from the support with a second configuration of at least one of the extension, the support or the transducer. For example, the extension may comprise a post 32SP, which post can be decoupled from the both the transducer 32 and the support 32S for removal of the transducer 32 and extension comprising post 32SP.

Figure 1F:
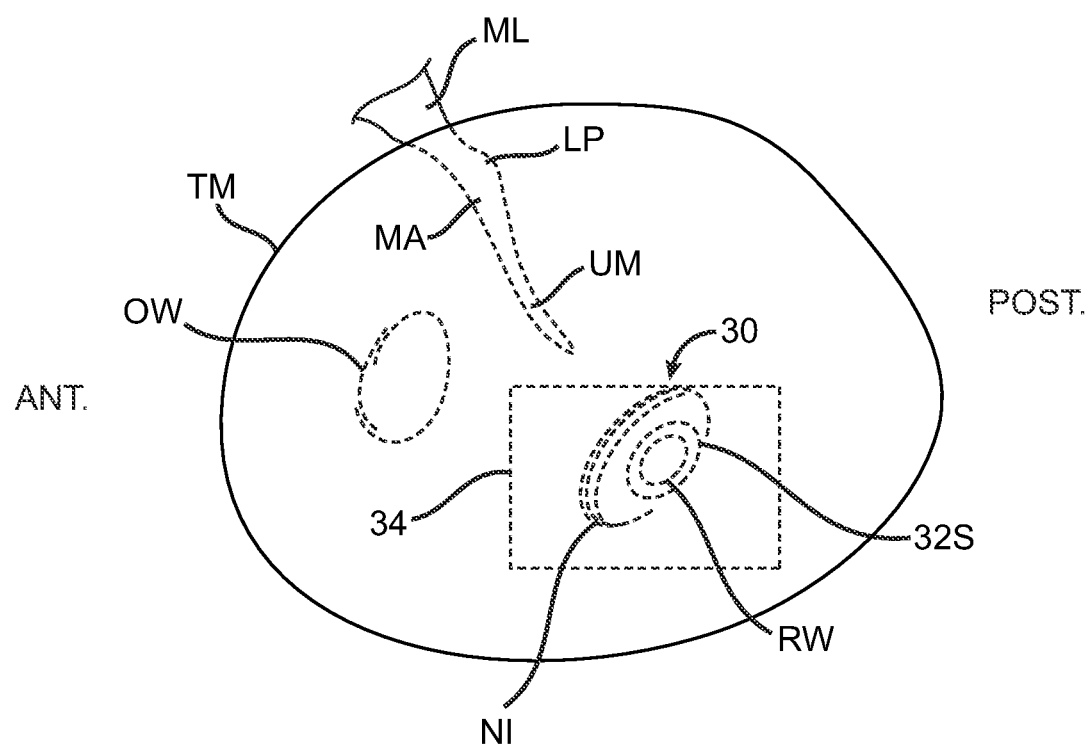
FIG. 1F shows a schematic illustration of a medial view of the output transducer assembly positioned in the middle ear of the user so as to couple to the round window as in FIGS. 1D to 1E3.

FIG. 1F shows a schematic illustration of a medial view the output transducer assembly positioned in the middle ear of the user so as to couple to the round window as in FIGS. 1D to 1E3. Assembly 30 is positioned in the middle ear behind eardrum TM. The at least one photodetector 34 is configured to receive electromagnetic radiation and is oriented toward eardrum TM. The at least one photodetector 34 can be positioned in the middle ear cavity so as to receive light energy transmitted through the posterior portion of the eardrum, for example through a posterior/inferior portion of the eardrum. The photodetector can be positioned over the round window niche so as to cover substantially the round window as seen from the medial view, corresponding to the path of light transmitted through the eardrum. The detector can be positioned about 0.5 mm to about 2 mm from the eardrum, and may comprise an optical coupler so as to couple to light energy transmitted through the eardrum. The support 32S can be positioned between the round window and at least one photo detector 34.

FIGS. 1G1 and 1G2 show side and top views of support 32S with first configuration to hold the magnet and barrier 32SB configured to inhibit tissue growth toward the magnet 32M. The barrier 32SB may comprise a material disposed so as to inhibit tissue growth toward the transducer comprising the magnet 32M. The barrier 32S may comprise known biocompatible materials with barrier properties, for example at least one of an elastomer, a biocompatible plastic, or a hydrogel. The support 32S may comprise a first side configured to couple to the round window RW and a second side configured to couple to the transducer such as magnet 32M. The barrier may extend in many ways along the second side to inhibit tissue contact at a location where the transducer such as magnet 32M couples to the support. For example the barriers 32S may extend along the second side away from the first side. The support may comprise structures such as holes 32SIG for tissue integration.

The support comprises at least one structure 32SR to couple the transducer to the support in a first configuration and to decouple the transducer from the support in a second configuration. For example, the structure may comprise biocompatible filaments that can be bent by a surgeon into a first configuration or a second configuration to couple the transducer to the support or decouple transducer from the support, respectively. The at least one structure 32SR can be bent inwardly over the magnet to retain the magnet. A person of ordinary skill in the art can determine additional structures having the first configuration to couple and the second configuration to decouple based on the teachings described herein.

FIG. 1G3 shows the support as in FIGS. 1G1 and 1G2 with a second configuration configured to release the magnet.

Figure 1H:
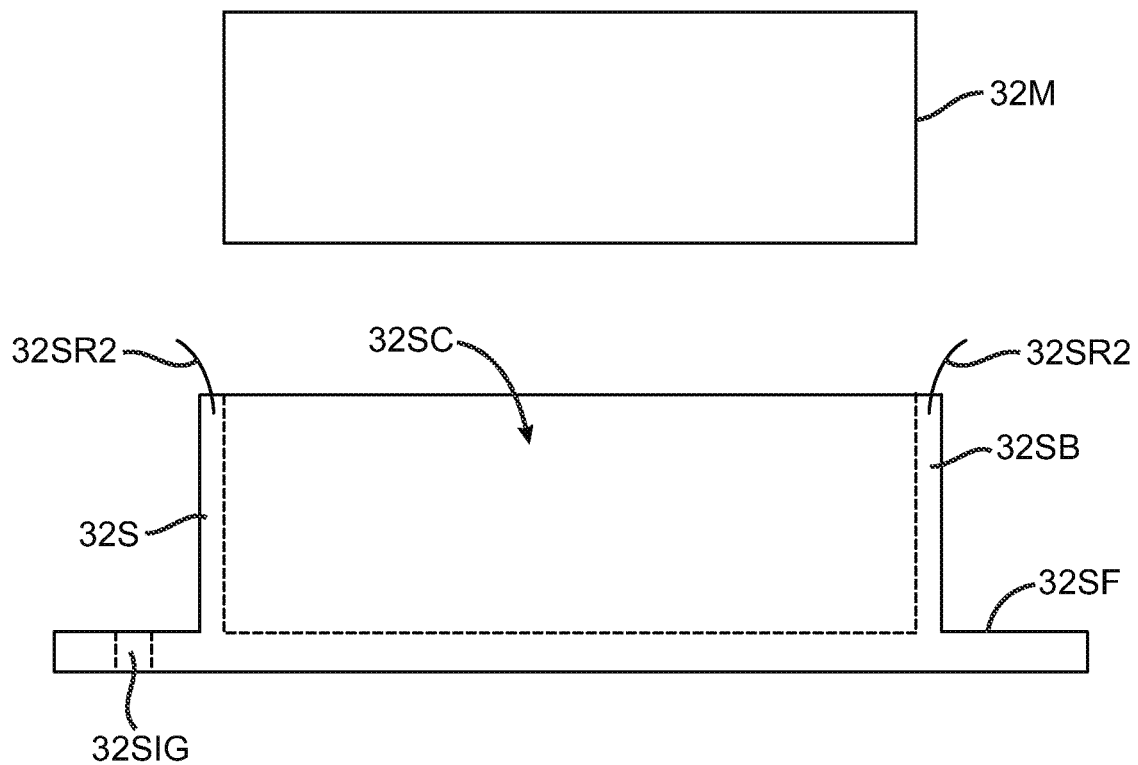
FIG. 1H shows support configured to hold the magnet with a first configuration, and barrier configured to inhibit tissue growth toward the magnet, in which the barrier extends laterally away from the magnet.
Figure 1H:

FIG. 1H shows support 32S configured to hold the magnet with a first configuration of at least one structure 32SR, and barrier 32SB configured to inhibit tissue growth toward the magnet, in which the barrier 32SB extends along the second side laterally away from the location of the support where the transducer such as the magnet couples to the support. The lateral extension of the support can be combined with extension away from the first side, as described above.

FIG. 1I1 shows support configured to hold the magnet with a first configuration, barrier configured to inhibit tissue growth and an annular structure sized to receive fascia to hold the support in place over the round window in accordance with embodiments.

FIG. 1I2 shows tissue structure of the round window suitable for coupling in accordance with embodiments of the present invention.

The support may be formed from a mold formed with premixed Dow Corning SILASTIC™ silicone elastomer medical grade MDX4-4210 (ten parts of base and one part of curing agent), for example. The magnet may be embedded in the polymer for example. In some embodiments, the support may be formed from a mold the user, for example a mold of the round window. The mold may include a portion of the tissue that defines the round window niche. The support can be formed from the mold of the user, such that the support is sized to the round window and the support may partially cover the round window. A person of ordinary skill in the art can conduct experiments based on the teaching herein to determine empirically the dimensions of the support to couple to the round window, and the extent of any advantages of molding the support to the round window of the user.

FIG. 1J shows magnet 32 of output assembly 30 comprising a pair of opposing magnets. The pair of opposing magnets comprises a first magnet 32M1 and a second magnet 32M2. The first magnet 32M1 and second magnet 32M2 are arranged such that the magnetic field of each magnet opposes the other magnet. This configuration can decrease sensitivity to external magnetic fields, for example transient magnetic fields that may increase user perceived noise and also decrease sensitivity to a magnetic fields from MRI machines, for example.

FIG. 1K shows an optical coupler comprising at least one optic 110 to couple to the light transmitted through the eardrum. The at least one optic 110 can be positioned over the at least one photodetector between the photodetector and the eardrum to improve coupling of the detector to the light transmitted through the eardrum. The at least one optic may comprise a substantially flat lower surface to couple to the at least one photodetector. The at least one optic 110 may comprise an array of lenslets such as spherical lenses, cylindrical lenses, and combinations thereof, for example.

FIG. 1L shows the at least one optic 110 of the coupler, in which the at least one optic 110 comprises a lens, in accordance with embodiments. The at least one optic may comprise a geometric shape corresponding to the shape of the eardrum to allow the optical coupler to be positioned near the eardrum to improve coupling efficiency of light transmitted through the eardrum. The at least one optic may comprise a lens, for example one or more of a convex lens, a concave lens, a spherical lens, an aspheric lens, a cylindrical lens, a toric lens, and combinations thereof. The shape may comprise one or more of many additional shapes that correspond to the eardrum, for example the posterior portion of the eardrum, and may comprise a shape corresponding to the medial side of the eardrum to position the surface of the optic close to the eardrum.

Human Eardrum Transmission Experiment

The below described experiment was conducted to measure transmission of infrared light through the eardrum and determine arrangements of the input assembly 20 and output assembly 30.

Objective: To determine the amount of light transmission loss through a human eardrum at posterior, inferior and anterior positions and the amount of scatter by the eardrum.

Procedure:

FIG. 2 shows the experimental set up to determine optical transmission through the tympanic membrane, in accordance with embodiments. A fiber optic coupled laser diode light source was aligned with a photodiode optical detector. An eardrum was placed in line and the change in optical output from the photodiode determined. The eardrum is mounted to a x,y,z translation stage which allows a change to different positions of the eardrum that the light goes through.

Materials:

Light source—1480 nm laser diode coupled to an optical fiber (250 um diameter, 80 um core);

PhotoDiode—1480 nm photodiode (5.5 mm2);

Load—RLC electrical circuit equivalent to that of a balanced armature transducer coupled to a diaphragm, which can be suitable for determining transmission through the eardrum.

Collimation optics and a Neutral Density Filter (NE20B);

DC Voltmeter (Fluke 8060A);

Translation stages; and

Human cadaver eardrum with attached malleus (incus and other medial components removed)

Results

No tympanic membrane

The current was set such that the photodiode was in the saturation region. A neutral density (ND) filter was used to attenuate the light output to reduced the PD response. The measurements indicate that the ND filter attenuated the light source by 20.5 dB. This ensured that all measurements reported are from the linear region.

The photodiode voltage in response to the collimated light beam without the eardrum was measured at the beginning of the measurements and at the end of experiment. The difference was less than 1%.

With no TM and ND filter, the output in mV was 349. With the ND filer and no TM, this output decreased to within a range from about 32.9 to 33.1, corresponding to a linear change of 0.095 and −20.5 dB.

With Tympanic Membrane

Measurements were made at anterior, inferior, and posterior positions of the eardrum. The eardrum was moved at different locations relative to the photodiode and it's distance X (in mm) approximated. Table 1 shows the measured voltages corresponding to the different positions and different eardrum locations.

TABLE 1

Measured photodiode voltages corresponding to transmission loss from the eardrum

| x (mm) | 0.1 | 0.5 | 1 | 2 | 3 |
|---|---|---|---|---|---|
| Posterior | 28 mV | 26.6 mV | 25.4 mV | 23.4 mV | 20.6 mV |
| Inferior | | | 23.6 mV | 21.1 mV | 17.1 mV |
| Anterior | | | 21.4 mV | 20.2 mV | 18.2 mV |

The posterior placement shows the highest voltage for all distances and has values of 28, 26.6, 25.4 23.4 and 20.6 for distances of 0.1, 0.5, 1, 2 and 3 mm, respectively.

For each eardrum position and location, the optical fiber was adjusted to maximize the PD voltage. This ensured that the light beam was maximally on the photodiode surface and that the measured response was due to transmission loss and not due to misalignments.

Calculations

The measured voltages were converted to percent transmission loss (hereinafter "TL") as follows:

% TL=$((V_{NoTM}-V_{WithTM})/V_{NoTM})*100$ where $V_{NoTM}$ is the measured voltage with no tympanic membrane and $V_{WithTM}$ is the measured voltage with the tympanic membrane Table 2 below shows the calculated % Transmission Loss using the above equation.

TABLE 2

% Transmission loss

| x (mm) | 0.1 | 0.5 | 1 | 2 | 3 |
|---|---|---|---|---|---|
| Posterior | 16 | 20 | 23 | 29 | 38 |
| Inferior | | | 29 | 36 | 48 |
| Anterior | | | 35 | 39 | 45 |
| Average | | | 29 | 35 | 44 |

At all locations the posterior placement showed the least transmission loss and values of 16, 20, 23, 29 and 38% at distances of 0.1, 0.5, 1, 2 and 3 mm, respectively.

With the PD very close to the eardrum (within about 0.1 mm), the TL is about 16%. The TL could only be measured for the Posterior position.

Of the three positions of the eardrum, the posterior position is better than the inferior position by 6-10%, and better than the anterior position by 7-12%.

As the eardrum is moved away from the PD, the transmission loss increases linearly for all three positions. The average transmission loss is about 29%, 35%, and 44% averaged across the three different positions for the 1, 2 and 3 mm locations respectively.

Experimental Conclusions

The transmission loss due to the eardrum is lowest at the posterior position (16%). The loss increases as the photodiode is moved away from the eardrum due to scatter of the collimated beam by the eardrum. At 3 mm from the eardrum, the average loss was as much as 44%. These data shown the unexpected result that there is more loss due to light scatter at angles away from the detector surface induced by the eardrum than due to transmission of light through the eardrum, and the detector and coupler such as a lens can be shaped appropriately so as to collect transmitted light scattered by the eardrum. These data also show the unexpected result that light transmission is higher through the posterior portion of the eardrum.

As the eardrum can move, the detector in a living person should be at least about 0.5 mm from the eardrum. The data suggest that a detector and/or component such as a lens can be shaped to fit the eardrum and provide improved transmission, for example shape with one or more of an inclined surface, a curved surface, and can be positioned within a range from about 0.5 mm to about 2 mm, for example.

The above data shows that illuminating a portion of the eardrum and placing a detector near the illuminated portion, for example can achieve transmission coupling efficiency between the projected light beam and detector of a least about 50% (corresponding to 50% loss), for example at least about 60% (corresponding to 40% loss). With posterior placement of the detector and illumination of a portion of the posterior region of the eardrum, the coupling efficiency can be at least about 70%, for example 80% or more. These unexpectedly high results for coupling efficiency indicate that illumination of a portion of the eardrum and a detector sized to the illuminated portion can provide efficiencies of at least about 50%. Also, the unexpected substantially lower transmission loss for the posterior portion of the eardrum as compared to each of the inferior and anterior portions indicates that transmission can be unexpectedly improved with posterior placement when most of the eardrum is illuminated. For example, the transmission coupling efficiency of the optical fiber to the photodetector can be improved substantially when the photodetector is positioned in the posterior portion of the middle ear cavity, for example the inferior posterior portion of the middle ear cavity, and an optical fiber is positioned in the ear canal without collimation optics such that light is emitted directly into the ear canal from the end of the optical fiber. Also, the high amount of light transmission through the eardrum shows that the optical signal can be transmitted through the eardrum, and that the sound encoded with the optically signal transmitted through the eardrum can stimulate the cochlea with vibration transmitted through the round window.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims and the full scope of the equivalents thereof.

What is claimed is:

1. A device to transmit user perceivable sound to an ear of a user, the ear having an eardrum, a middle ear, an ossicular chain within the middle ear, and a round window membrane located within a round window niche, the device comprising:

a support configured to couple to the round window membrane, the support sized for placement on the round window membrane located within the round window niche; and a transducer configured to reside entirely within the middle ear and to receive a signal representative of the user perceivable sound transmitted wirelessly through the eardrum from an input, wherein the transducer is further configured to affix to an anatomical structure within the middle ear without contacting the ossicular chain within the middle ear when the transducer is positioned in the middle ear medial to the eardrum and to couple to the round window membrane through the support when the support is placed on the round window membrane in order to transmit the sound solely in response to the received signal, wherein the input is configured to receive the user perceivable sound from an ambient environment, process the received user perceivable sound to generate the signal, and transmit the signal to the transducer.

2. The device of claim 1, wherein the support is disposed at least partially between the transducer and the round window membrane to inhibit contact of the transducer and round window membrane.

3. The device of claim 1, wherein the support is configured to decouple from round window membrane without tearing tissue of the round window membrane.

4. The device of claim 1, wherein the support is configured to be able to be decoupled from the transducer when the support is affixed to the round window membrane.

5. The device of claim 4 wherein the support is configured to affix to the round window membrane, and wherein the support is configured to decouple from the transducer to remove the transducer from the middle ear when the support is affixed to the round window membrane.

6. The device of claim 4 wherein the support comprises a first side to couple to the round window membrane and a second side opposite the first side to couple to the transducer.

7. The device of claim 6, wherein the support comprises an extension extending along the second side to inhibit tissue growth toward the transducer.

8. The device of claim 7, wherein the extension extends along the second side parallel to the first side.

9. The device of claim 7, wherein the extension extends away from the first side along the transducer.

10. The device of claim 7, wherein the second side of the support comprises a recess sized to receive at least a portion of the transducer.

11. The device of claim 4, wherein the support comprises a structure configured to hold the transducer with a first configuration and release the transducer with a second configuration.

12. The device of claim 11, wherein the structure comprises an extension configured to extend from the support to the transducer, and wherein the extension is further configured to be able to be decoupled from the transducer to release the transducer.

13. The device of claim 4, wherein the support comprises a first side configured to couple to the round window membrane and a second side configured to couple to the transducer.

14. The device of claim 13, wherein the support comprises a first configuration to couple to the transducer and a second configuration to decouple from the transducer.

15. The device of claim 1, wherein the support comprises a soft biocompatible material configured to conform to the round window membrane.

16. The device of claim 15, wherein the support comprises a thin flexible material configured to deform with the round window membrane in response to the sound.

17. The device of claim 15, wherein the support is composed of a material comprising at least one of collagen, silicone, hydrogel, biocompatible plastic, or elastomer.

18. The device of claim 1, wherein the support is configured to couple to a mucosal tissue disposed over the round window membrane.

19. The device of claim 1, wherein the support is configured to couple to the round window membrane with a liquid.

20. The device of claim 19, wherein the liquid comprises an oil.

21. The device of claim 1, wherein the transducer comprises at least one of a magnet, a coil, the coil and the magnet, a piezoelectric transducer, a photostrictive transducer, a balanced armature transducer or a magnetostrictive transducer.

22. The device of claim 21, wherein the transducer comprises the magnet and wherein the magnet is coupled to the support.

23. The device of claim 22, wherein the support comprises a first side configured to couple to the round window membrane and a second side coupled to the magnet.

24. The device of claim 23, wherein the support comprises a first configuration to couple to the magnet and a second configuration to release the magnet.

25. The device of claim 22, wherein the transducer comprises the coil and wherein the coil is configured for placement in the middle ear of the user to couple to the magnet on the support.

26. The device of claim 21, wherein the transducer comprises the balanced armature transducer and wherein a reed of the balanced armature transducer is coupled to the support to vibrate the round window membrane.

27. The device of claim 26, wherein a structure extends from the reed to the support to couple the balanced armature transducer to the support in a first configuration.

28. The device of claim 27, wherein the structure extending from the reed to the support is configured to decouple from at least the support in a second configuration to remove the balanced armature transducer from the middle ear of the user.

29. The device of claim 26 wherein the input comprises a light source to transmit light energy along an ear canal through the eardrum, and wherein the device further comprises a photodetector sized for placement in the middle ear and coupling to the balance armature transducer to transmit the sound to the user.

30. The device of claim 1, further comprising an anchor coupled to the transducer to affix the transducer to the anatomical structure within the middle ear of the user.

31. The device of claim 1, wherein the transducer has a cross-sectional size to pass through an incision made in the eardrum and an annulus of the ear of the user, the incision being made such that bone defining an ear canal of the user remains intact.

32. The device of claim 1, wherein the input comprises a light source to transmit the signal as light energy along an ear canal of the user through the eardrum, and wherein the device further comprises a photodetector sized for placement in the middle ear and coupled to the transducer to transmit the sound to the user.

33. A method of transmitting user perceivable sound to an ear of a user, the ear having an eardrum, a middle ear, an ossicular chain within the middle ear, and a round window membrane located within a round window niche, the method comprising:

receiving the user perceivable sound from an ambient environment;

processing the received user perceivable sound to generate a signal representative of the user perceivable sound;

transmitting the signal wirelessly through the eardrum to a transducer coupled to a support placed on the round window membrane located within the round window niche; and vibrating the round window membrane with the transducer through the support placed on the round window membrane solely in response to the wireless signal, wherein the transducer is positioned entirely in a middle ear medial to the eardrum without contacting the ossicular chain within the middle ear and affixed to an anatomical structure within the middle ear.

34. A method of providing a hearing prosthesis to transmit user perceivable sound to an ear of a user, the ear having an eardrum, a middle ear, an ossicular chain within the middle ear, and a round window membrane located within a round window niche, the method comprising:

positioning a transducer entirely in a middle ear of the user medial to the eardrum and affixing the transducer to an anatomical structure within the middle ear, wherein the transducer is positioned in the middle ear without contacting the ossicular chain within the middle ear; and placing a support on the round window membrane located within the round window niche, such that the transducer is coupled to the round window membrane through the support placed on the round window niche to transmit the sound to the user, wherein the transducer is configured to receive a signal representative of the user perceivable sound transmitted wirelessly through the eardrum from an input and transmit the user perceivable sound solely in response to the received signal, and wherein the input is configured to receive the user perceivable sound from an ambient environment, process the received user perceivable sound to generate the signal, and transmit the signal to the transducer.

35. The method of claim 34 wherein the transducer contacts the support and the support is configured to separate from the transducer.

36. The method of claim 34 wherein the support comprises a non-magnetic material.

37. The method of claim 34, wherein the anatomical structure within the middle ear to which the transducer is affixed is a bone of a promontory of the middle ear.

* * * * *